(12) United States Patent
Frostegård

(10) Patent No.: US 10,752,680 B2
(45) Date of Patent: Aug. 25, 2020

(54) ANTIBODIES AGAINST PHOSPHORYLCHOLINE IN COMBINATION THERAPY WITH BIOLOGIC AGENTS

(71) Applicant: Athera Biotechnologies AB, Stockholm (SE)

(72) Inventor: Johan Frostegård, Stockholm (SE)

(73) Assignee: ATHERA BIOTECHNOLOGIES AB, Stockholm (SE)

(*) Notice: Subject to any disclaimer, the term of this patent is extended or adjusted under 35 U.S.C. 154(b) by 503 days.

(21) Appl. No.: 15/150,039

(22) Filed: May 9, 2016

(65) Prior Publication Data

US 2016/0251427 A1  Sep. 1, 2016
US 2018/0186870 A9  Jul. 5, 2018

Related U.S. Application Data

(62) Division of application No. 13/582,193, filed as application No. PCT/EP2011/001090 on Mar. 4, 2011, now abandoned.

(60) Provisional application No. 61/349,410, filed on May 28, 2010, provisional application No. 61/310,519, filed on Mar. 4, 2010.

(51) Int. Cl.

| C07K 16/24 | (2006.01) |
| A61K 39/395 | (2006.01) |
| C07K 16/28 | (2006.01) |
| A61K 35/28 | (2015.01) |
| C07K 14/525 | (2006.01) |
| C07K 16/18 | (2006.01) |
| A61K 39/00 | (2006.01) |

(52) U.S. Cl.
CPC .......... *C07K 16/241* (2013.01); *A61K 35/28* (2013.01); *A61K 39/39533* (2013.01); *C07K 14/525* (2013.01); *C07K 16/18* (2013.01); *C07K 16/2887* (2013.01); *A61K 2039/505* (2013.01); *C07K 2317/21* (2013.01); *C07K 2317/24* (2013.01); *C07K 2319/30* (2013.01)

(58) Field of Classification Search
None
See application file for complete search history.

(56) References Cited

U.S. PATENT DOCUMENTS

| 8,012,483 B2 | 9/2011 | De Faire et al. | |
| 2008/0160020 A1* | 7/2008 | Silverman | C07K 16/44 424/133.1 |
| 2011/0206679 A1 | 8/2011 | Frostegard et al. | |

OTHER PUBLICATIONS

Lederman et al. (Molecular Immunology 28: 1171-1181, 1991).*
Li et al. (PNAS 77: 3211-3214, 1980).*
Elkan et al. (Arthritis Research and Therapy 2009 11(2):R37).*
Perdriger et al. (Biologics 2009, 3:183-191).*
Snowden et al. (The Journal of Rheumatology 2004, 31:482-488).*
International Search Report for PCT/EP2011/001090 dated Aug. 17, 2011.
Weinblatt, M. E., et al., "RAPID: Rheumatoid Arthritis", *J Fam Pract.* 2007, vol. 56, (4 Suppl), S1-7; quiz S8.
Meune, C., et al., "Trends in Cardiovascular Mortality in Patients with Rheumatoid Arthritis Over 50 Years: A Systematic Review and Meta-Analysis of Cohort Studies", *Rheumatology (Oxford)*, 2009, vol. 48, No. 10, pp. 1309-1313.
Peters, M. J., et al., "Does Rheumatoid Arthritis Equal Diabetes Mellitus as an Independent Risk Factor for Cardiovascular Disease", A prospective study. *Arthritis Rheum*, 2009, vol. 61, No. 11, pp. 1571-1579.
Frostegard, J., "Atherosclerosis in Patients with Autoimmune Disorders", *Arterioscler Thromb Vasc Biol*, 2005, vol. 25, No. 9, pp. 1776-1785.
Cugno, M., et al., "Potential Effect of Anti-Tumour Necrosis Factor-Alpha Treatment on Reducing the Cardiovascular Risk Related to Rheumatoid Arthritis", *Curr Vasc Pharmacol*, Mar. 2010, vol. 8, No. 2, 285-92.
Maki-Petaja, K. M., et al., "Rheumatoid Arthritis is Associated with Increased Aortic Pulse-Wave Velocity, Which is Reduced by Anti-Tumor Necrosis Factor-Alpha Therapy", *Circulation*. 2006, vol. 114, No. 11, pp. 1185-1192.
Van Doornum, S., et al., "Tumour Necrosis Factor Antagonists Improve Disease Activity but not Arterial Stiffness in Rheumatoid Arthritis", *Rheumatology (Oxford)*. 2005, vol. 44, No. 11, pp. 1428-1432.
Garces, S. P., et al., "Anti-tumour Necrosis Factor Agents and Lipid Profile: A Class Effect", *Ann Rheum Dis.*, 2008, vol. 67, No. 6, pp. 895-896.
Soubrier, M., et al., "Effects of Anti-Tumor Necrosis Factor Therapy on Lipid Profile in Patients with Rheumatoid Arthritis", *Joint Bone Spine*, 2008, vol. 75, No. 1, pp. 22-24.
Dorner, T., et al., "B-cell-Directed Therapies for Autoimmune Disease", *Nat Rev Rheumatol.*, 2009, vol. 5, No. 8, 433-441.
Wu, R., et al., Autoantibodies to OxLDL are Decreased in Individuals with Borderline Hypertension. *Hypertension.* 1999, vol. 33, No. 1, pp. 53-59.
Binder, C. J., et al, "Natural Antibodies and the Autoimmunity of Atherosclerosis", *Springer Semin Immunopathol*, 2005, vol. 26, No. 4, pp. 385-404.

(Continued)

*Primary Examiner* — Sharon X Wen
(74) *Attorney, Agent, or Firm* — Stephen J. Weyer, Esq.; Stites & Harbison, PLLC

(57) ABSTRACT

Antibodies against PC, PC conjugate or bioactive components and/or fragments thereof for use in combination therapy with one or more biologic agents and/or stem cells are disclosed, as well as compositions comprising the antibodies in combination with one or more biologic agents and/or stem cells. Also disclosed are PC conjugates, PC or bioactive components and/or parts/fragments thereof for use in activation immunotherapy prior to or in combination with treatment with biologic agents and/or stem cells for curing, treating, preventing, and/or reducing the risk of developing auto-immune diseases, chronic inflammatory diseases, and cancer diseases, as well as compositions comprising them in combination with biologic agents and/or stem cells.

2 Claims, 5 Drawing Sheets

(56) References Cited

OTHER PUBLICATIONS

Shoenfeld, Y., et al., "Are Anti-Oxidized Low-Density Lipoprotein Antibodies Pathogenic or Protective?", *Circulation*. 2004, vol. 110, No. 17, pp. 2552-2558.
Kerekes, G., et al., "Effects of Rituximab Treatment on Endothelial Dysfunction, Carotid Atherosclerosis, and Lipid Profile in Rheumatoid Arthritis", *Clin Rheumatolm*, 2009, vol. 28, No. 6, pp. 705-710.
Jin, T., et al., "Impact of Short-Term Therapies with Biologics on Prothrombotic Biomarkers in Rheumatoid Arthritis", *Clin Exp Rheumatol*, 2009, vol. 27, No. 3, pp. 491-494.
Gronlund, H., et al., "Low Levels of IgM Antibodies Against Phosphorylcholine Predict Development of Acute Myocardial Infarction in a Population-Based Cohort from Northern Sweden", *Eur J Cardiovasc Prev Rehabil*, 2009.
Elkan, A. C., et al., "Gluten-Free Vegan Diet Induces Decreased LDL and Oxidized LDL Levels and Raised Atheroprotective Natural Antibodies Against Phosphorylcholine in Patients with Rheumatoid Arthritis: a Randomized Study", *Arthritis Res Ther*, 2008, vol. 10, No. 2, p. R34.
De Faire, U., et al., "Low Levels of IgM Antibodies to Phosphorylcholine Predict Cardiovascular Disease in 60-Year Old Men: Effects on Uptake of Oxidized LDL in Macrophages as a Potential Mechanism", *J Autoimmun*, London, GB, vol. 34, No. 2, (Mar. 1, 2010), pp. 73-79.
Su, J., et al., Antibodies of IgM Subclass to Phosphorylcholine and Oxidized Ldl are Protective Factors for Atherosclerosis in Patients with Hypertension, *Atherosclerosis*, 2006, vol. 188, No. 1, pp. 160-166.
Su, J., et al., "Natural Antibodies Against Phosphorylcholine as Potential Protective Factors in SLE", *Rheumatology (Oxford)*, 2008, vol. 47, No. 8, pp. 1144-1150.
Cornec, D., et al., "Critical Analysis of Rituximab-Induced Serological Changes in Connective Tissue Diseases", *Autoimmun Rev*, 2009, vol. 8, No. 6, pp. 515-519.
Briles, D. E., et al., "Anti-Phosphorylcholine Antibodies of the T15 Idiotype are Optimally Protective Against *Streptococcus pneumoniae*" *J Exp Med.*, 1982; 156, No. 4, pp. 1177-1185.
Harnett W, et al., "Phosphorylcholine: Friend or Foe of the Immune System", *Immunol Today*. 1999, vol. 20, No. 3, pp. 125-129.
Frostegard J., et al., "Atheroprotective Natural Anti-Phosphorylcholine Antibodies of IgM Subclass are Decreased in Swedish Controls as Compared to Non-Westernized Individuals from New Guinea", *Nutr Metab (Lond)*, 2007, vol. 4, No. 1, p. 7.
Caligiuri G, et al., "Phosphorylcholine-Targeting Immunization Reduces Atherosclerosis", *J Am Coll Cardiol*, 2007, vol. 50, No. 6, pp. 540-546.
Faria-Neto J. R., et al., "Passive Immunization with Monoclonal IgM Antibodies Against Phosphorylcholine Reduces Accelerated Vein Graft Atherosclerosis in Apolipoprotein E-null Mice", *Atherosclerosis*. 2006;189(1):83-90.
Edwards L. J., "Platelet Activating Factor/Platelet Activating Factor Receptor Pathway as a Potential Therapeutic Target in Autoimmune Diseases", *Inflamm Allergy Drug Targets*, 2009, vol. 8 No. 3, pp. 182-190.
Gonzalez-Juanatey, C, et al., "Short-term Improvement of Endothelial Function in Rituximab-Treated Rheumatoid Arthritis Patients Refractory to Tumor Necrosis Factor Alpha Blocker Therapy", *Arthritis Rheum*, 2008, vol. 59, No. 12, pp. 1821-1824.
Reff, M. E., et al., "Depletion of B Cells in Vivo by a Chimeric Mouse Human Monoclonal Antibody to CD20", *Blood*, 1994, vol. 83, No. 2, pp. 435-445.
Van Leeuwen, M. et al,. "The Therapeutic Potential of Targeting B Cells and Anti-oxLDL Antibodies in Atherosclerosis", *Autoimmun Rev*, 2009, vol. 9, No. 1, pp. 53-57.
Cambridge, G. et al., "B Cell Depletion Therapy in Systemic Lupus Erythematosus: Effect on Autoantibody and Antimicrobial Antibody Profiles", *Arthritis Rheum*, 2006, vol. 54, No. 11, pp. 3612-3622.
Frostegard, J. et al., "Induction of T-cell Activation by Oxidized Low Density Lipoprotein", *Arterioscler Thromb*, 1992, vol. 12, No. 4, pp. 461-467.
Winyard, P.G., et al., "Presence of Foam Cells Containing Oxidized Low Density Lipoprotein in the Synovial Membrane from Patients with Rheumatoid Arthritis", *Ann Rheum Dis*. 1993, vol. 52, No. 9, pp. 677-680.
Suzuki, T, et al., "Diagnostic Implications of Circulating Oxidized Low Density Lipoprotein Levels as a Biochemical Risk Marker of Coronary Artery Disease" *Clin Biochem*. 2002 vol. 35 No. 5, pp. 347-353.
Itabe, Hiroyuki, et al., Measurement of Plasma Oxidized Low-Density Lipoprotein and its Clinical Implications, *J. Atheroscler Thromb*. 2007;14(1):1-11.
Holme Ingar, et al., "Lipoprotein Components and Risk of Congestive Heart Failure in 84,740 Men and Women in the Apolipoprotein Mortality Risk Study (AMORIS)", *Eur J Heart Fail*. 2009, vol. 11, No. 11, pp. 1036-1042.
Walldius G. et al., "Rationale for Using Apolipoprotein B and Apolipoprotein A-I as Indicators of Cardiac Risk and as Targets for Lipid-Lowering Therapy" *Eur Heart J.*, 2005 vol. 26, No. 3, pp. 210-212.
Choy E., et al., "Interpreting Lipid Levels in the Context of High-Grade Inflammatory States with a Focus on Rheumatoid Arthritis: a Challenge to Conventional Cardiovascular Risk Actions", *Ann Rheum Dis.*, 2009, vol. 68, No. 4, pp. 460-469.
Jacobsson Lennart T. H., et al., Treatment with TNF blockers and mortality risk in patients with rheumatoid arthritis. *Ann Rheum Dis*. 2007;66(5):670-675.
Arnett, Frank C. et al., "The American Rheumatism Association 1987 Revised Criteria for the Classification of Rheumatoid Arthritis", *Arthritis Rheum.*, 1988 vol. 31, No. 3 pp. 315-324.
Prevoo M. L. L., et al., "Modified Disease Activity Scores that Include Twenty-Eight-Joint Counts. Development and Validation in a Prospective Longitudinal Study of Patients with Rheumatoid Arthritis", *Arthritis Rheum.*, 1995, vol. 38, No. 1 pp. 44-48.
Ekdahl C. et al,. "Assessing Disability in Patients with Rheumatoid Arthritis. Use of a Swedish Version of the Stanford Health Assessment Questionnaire", *Scand J Rheumatol*. 1988 vol. 17, No. 4, pp. 263-271.
Sjoberg, BG, et al., "Low Levels of IgM Antibodies Against phosphorylcholine—A Potential Risk Marker for Ischemic Stroke in Men", *Atherosclerosis*, 2009, vol. 203, No. 2, pp. 528-532.
Zanchetti, A., et al., "Risk Factors Associated With Alterations in Carotid Intima-Media Thickness in Hypertension: Baseline Data From the European Lacidipine Study on Atherosclerosis", *J Hypertens.*, 1998, vol. 16, No. 7, pp. 949-961.
Zanchetti, A, et al., "Calcium Antagonist Lacidipine Slows Down Progression of Asymptomatic Carotid Atherosclerosis: Principal Results of the European Lacidipine Study on Atherosclerosis (ELSA), a Randomized, Double-Blind, Long-Term Trial.", *Circulation*. 2002, vol. 106, No. 19, pp. 2422-2427.
Carlsson, A C., et al., "Risk Factors Associated with Newly Diagnosed High Blood Pressure in Men and Women". Am J Hypertens. 2008;21(7):771-777.
Halldin, M, et al., "The metabolic syndrome: prevalence and association to leisure-time and work-related physical activity in 60-year-old men and women", Nutr Metab Cardiovasc Dis. 2007;17(5): pp. 349-357.
Frostegard Johan, "Low Level Natural Antibodies Against Phosphorylcholine: A Novel Risk Marker and Potential Mechanism in Atherosclerosis and Cardiovascular Disease" *Clinical Immunology* (Orlando, Fla.) Jan. 2010, vol. 134, No. 1, (Jan. 2010), pp. 47-54.
De Faire, Ulf et al., "Natural Antibodies Against Phosphorylcholine in Cardiovascular Disease" *Annals of the New York Academy of Sciences*, Sep. 2009, vol. 1173, (Sep. 2009), pp. 292-300.
Fiskesund, Roland et al., "Low Levels of Antibodies Against Phosphorylcholine Predict Development of Stroke in a Population-Based Study from Northern Sweden" Stroke; A Journal of Cerebral Circulation, Apr. 2010, vol. 41, No. 4, (Feb. 11, 2010), pp. 607-612.

(56) References Cited

OTHER PUBLICATIONS

Lewis, Myles J. et al., "Immunoglobulin M is Required for Protection Against Atherosclerosis in Low-Density Lipoprotein Receptor-Deficient Mice" *Circulation* Aug. 4, 2009, vol. 120, No. 5, (Aug. 4, 2009), pp. 417-426.

Listing Joachim et al., "Does Tumor Necrosis Factor a Inhibition Promote or Prevent Heart Failure in Patients with Rheumatoid Arthritis" *Arthritis & Rheumatism*, vol. 58, No. 3, Mar. 2008 (Mar. 2008),pp. 667-677.

Gokalves, Isabel et al., "Identification of the Target for Therapeutic Recombinant anti-apoB-100 Peptide Antibodies in Human Atherosclerotic Lesions." *Atherosclerosis*, Jul. 2009, vol. 205, No. 1,(Jul. 2009),pp. 96-100.

Sofia Ajeganova, et al., "TNF and Natural Atheroprotective Antibodies Against Phosphorylcholine: Implications for Biologics in RA.", *Arthritis & Rheumatism*, vol. 62, No. Suppl 10, 2010, p. 88.

Spira et al. T15 PC Binding Monoclonal Antibodies Retain Specificity When They Switch From IgM to IgG. *J. Immunology*, 140 (1988), pp. 2675-2680.

Kim et al., "I-PLA$_2$ Activation during Apoptosis Promotes the Exposure of Membrane Lysophosphatidylcholine Leading to Binding by Natural Immunoglobulin M Antibodies and Complement Activation.", *J Exp Med.*, vol. 196, (2002), pp. 655-665.

\* cited by examiner

Figure 2, Panel A
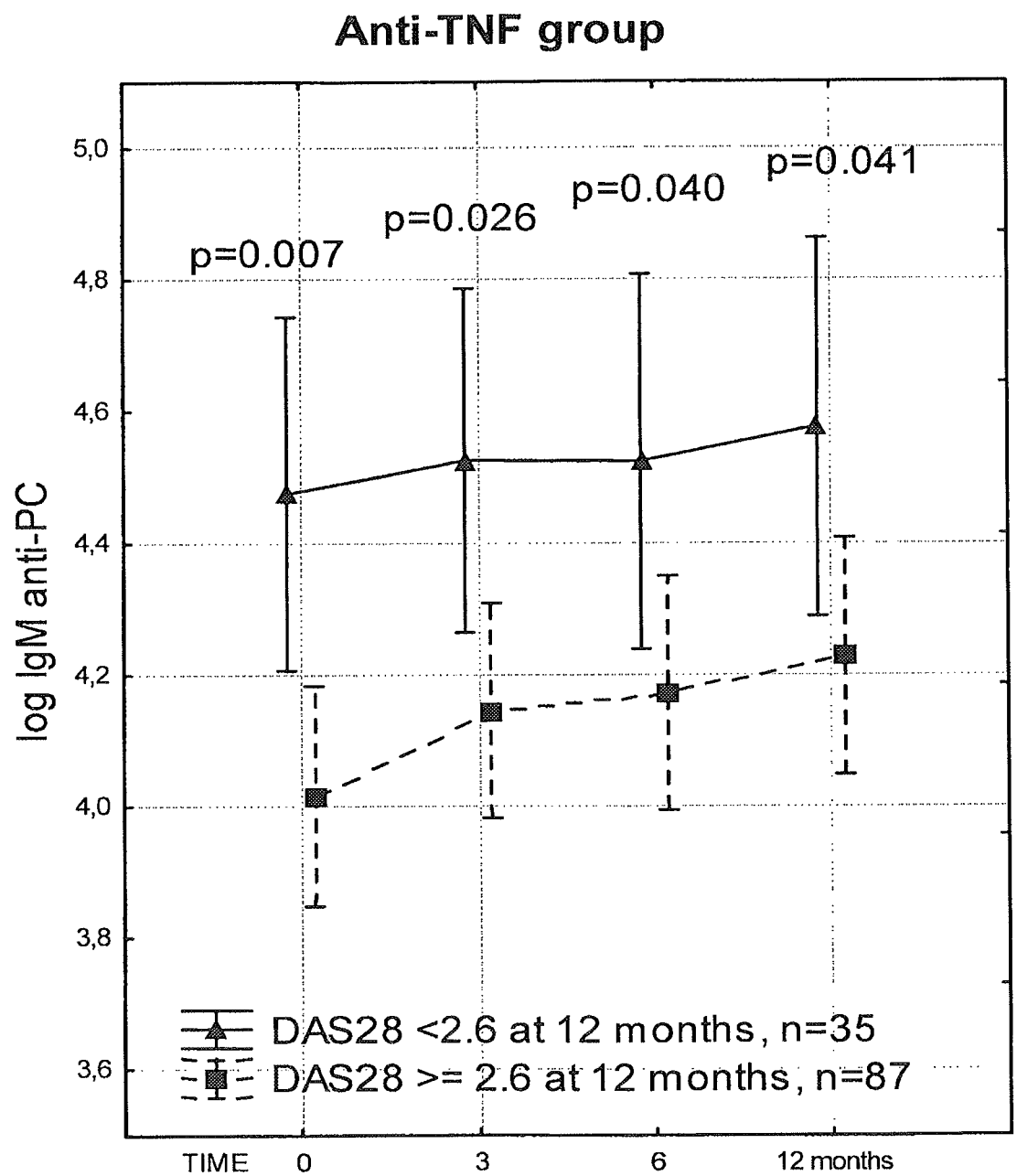

Figure 2, Panel B
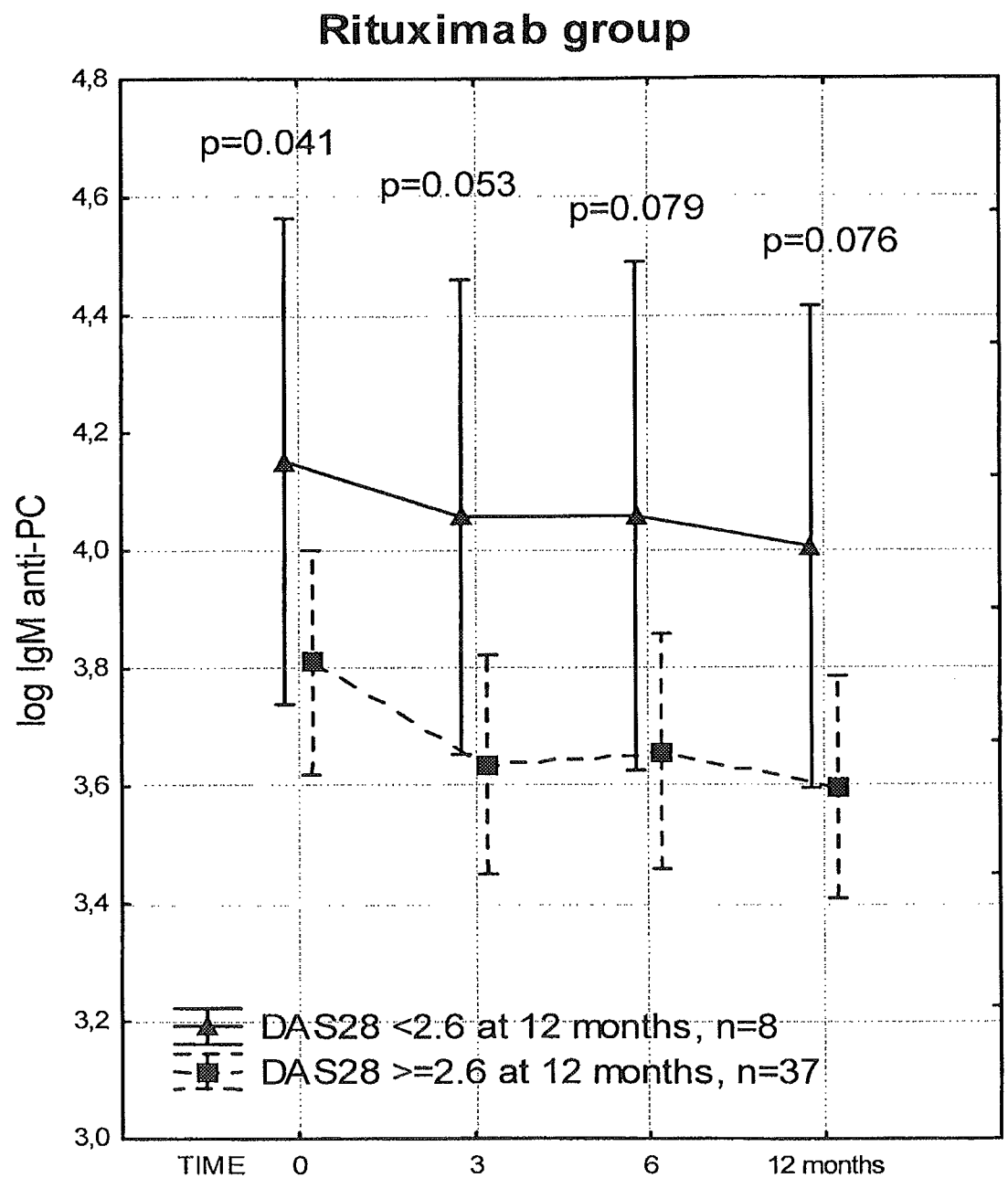

ANTIBODIES AGAINST PHOSPHORYLCHOLINE IN COMBINATION THERAPY WITH BIOLOGIC AGENTS

CROSS REFERENCE TO RELATED APPLICATIONS

This application is a divisional application of U.S. Ser. No. 13/582,193, having a filing date of Aug. 31, 2012, which was a 371 application of International application PCT/EP2011/001090, filed Mar. 4, 2011, which claimed the benefit of U.S. provisional patent applications 61/310,519, filed Mar. 4, 2011 and 61/349,410, filed May 28, 2010, all of said applications incorporated herein by reference.

FIELD OF THE INVENTION

This invention relates to antibodies against PC, PC conjugate or bioactive components and/or fragments thereof for use in combination therapy with one or more biologic agents and/or stem cells in a mammal, as well as to compositions comprising the antibodies in combination with one or more biologic agents and/or stem cells. It also relates to PC conjugates, PC or bioactive components and/or parts/fragments thereof for use in activation immunotherapy in a mammal prior to or in combination with the treatment of a mammal with biologic agents and/or stem cells for curing, treating, preventing, and/or reducing the risk of developing autoimmune diseases, chronic inflammatory diseases, and cancer diseases, as well as compositions comprising them in combination with biologic agents and/or stem cells. It also relates to the use of antibodies against phosphorylcholine (PC), PC conjugate or bioactive components and/or fragments thereof in combination therapy with one or more biologic agents and/or stem cells in a mammal, as well as their use in the preparation of a medicament for use in such therapy.

BACKGROUND OF THE INVENTION

Chronic inflammatory, autoimmune, and cancer diseases are major health problems in the Western world and becoming increasingly so in developing countries. These diseases include rheumatic conditions, such as rheumatoid arthritis (RA) and systemic lupus erythematosus (SLE). The latter is often described as a prototypic systemic autoimmune disease, and more than 80 autoimmune rheumatic diseases have been described, cf. e.g. Harrison's Principles of Internal Medicine, 17th Edition.

Rheumatoid arthritis is a chronic inflammatory disease that affects 0.5-1% of the general population[1]. Cardiovascular disease (CVD) represents a major source of serious morbidity and mortality and accounts for an increase in risk of approximately 60% for all RA-related deaths[2]. Recently it was suggested that RA may be equal to diabetes mellitus type 2 as an independent risk factor for CVD[3]. Traditional Framingham risk factors and inflammation-associated factors may contribute to increased risk of CVD in RA[4].

Cancer diseases represent a substantial challenge to the health care system and communities due to the high costs associated with treatment. The majority of patients experience a decrease of life quality during treatment. Some of the cancer diseases may be treated by biologic agents, which may be associated with side effects.

In recent years, the treatment of RA has improved due to the introduction of biologics, including tumor necrosis factor (TNF) antagonists and B-cell-targeting agents such as rituximab. Several studies consistently indicate that anti-TNF treatment ameliorates the risk of CVD[5]. The effect of TNF blockade on the cardiovascular functions, such as, for example, arterial stiffness, is not clear, and there are both positive[6] and negative studies[7]. In addition, suppression of inflammation in RA by TNF blockade has been shown to induce pro-atherogenic changes in lipid profiles[8], but data on short-term and long-term effects remain inconsistent[9].

Rituximab inhibits B-cell function by targeting CD20, and is increasingly used in rheumatic and autoimmune diseases, including RA, especially for treatment of patients who do not respond to anti-TNF treatment[10]. Little is known about the exact role of B cells in CVD and atherosclerosis, but both pro- and anti-atherogenic effects have been suggested[11-13]. Recent studies indicate that short-term treatment with rituximab improves vascular function and dyslipidemia[14]; moreover, it decreases pro-thrombotic biomarkers[15]. Thus, anti-CD20 treatment may reduce future CVD risks in RA, but data are limited.

It has recently been reported that low levels of IgM natural antibodies against phosphorylcholine (anti-PC) independently predict CVD[16-18] and that there is a negative association between anti-PC levels and development of human atherosclerosis[19]. Further, low levels of IgM anti-PC were associated with systemic lupus erythematosus (SLE) in a nested case-control SLE-study[20]. No studies addressing anti-PC in RA and effects of anti-TNF treatment have been performed. Anti-CD20 treatment has been shown to decrease total immunoglobulin, mostly IgM, and to induce heterogeneous effects on antibody levels in rheumatic diseases[21]. The effects of B-cell depletion on anti-PC levels are still not known.

It is here reported how treatment with biologic agents, such as etanercept, infliximab, adalimumab and rituximab, during one year influences levels of IgM anti-PC, oxidized low-density lipoprotein (oxLDL) and the apolipoprotein profile.

SUMMARY OF THE INVENTION

In summary, low levels of anti-PC predict a lack of response to treatment with biologics in RA. It has previously been demonstrated that anti-PC have anti-inflammatory properties by inhibiting effects of inflammatory phospholipids like PAF[20]. This finding indicates that treatment to inhibit such inflammatory reactions promoted by inflammatory phospholipids could potentiate the effect of biologics.

One important finding according to the present invention is that natural antibodies against an epitope in the phospholipid moiety of membranes including oxLDL, IgM phosphorylcholine (anti-PC), increased during one year treatment of RA with TNF inhibitors, but decreased when patients were treated with rituximab, a B-cell inhibitor. These observations may have several implications.

Anti-PC are natural antibodies, which were described in early studies as being of major importance in the early response to lethal infections with PC-exposing Meningococcae in mice[22]. PC may play different roles in immune reactions, which may be both protective and deleterious[23].

It has been suggested that anti-PC are atheroprotective in humans, since anti-PC are negatively associated with atherosclerosis development[19]. Further, low anti-PC levels are independently associated with increased risk of CVD[16-18]. Also, it has previously been reported that individuals from Kitava, New Guinea, with a traditional life-style, have high anti-PC levels. Interestingly, these individuals do not seem to suffer from CVD and only to a very limited degree from rheumatic diseases[24]. In line with clinical studies, mice experiments indicate that both active and passive immunization with anti-PC lead to decreased development of atherosclerosis[25,26].

Without being bound by theory, there appear to be three potential mechanisms by which anti-PC could protect against cardiovascular disease. Firstly, anti-PC have anti-inflammatory and inhibiting effects on inflammatory phospholipids, such as platelet activating factor (PAF)[20]. Another mechanism could be inhibition of macrophage uptake of oxLDL by anti-PC[18]. Increased levels of anti-PC could in principle ameliorate disease manifestations through inhibition of PAF, with implications for chronic inflammatory diseases in general[27]. A third mechanism could be prevention of plaque rupture by the inhibition of the cytotoxic effects of lysophosphatidylcholine, with implications for acute cardiovascular diseases in particular.

The effect of anti-PC IgM on the cytotoxic effects of lysophosphatidylcholine was investigated, and anti-PC IgM was found to reduce cell death in 2 different assays, thus lending support to the concept that anti-PC IgM could prevent plaque rupture by the inhibition of the cytotoxic effects of lysophosphatidylcholine.

Based on these findings, a novel hypothesis according to which low levels of anti-PC represent an immunodeficient state, thereby increasing risk of chronic inflammatory, autoimmune and cancer diseases, is provided according to the present invention. In this aspect, our finding that anti-PC levels were significantly lower among non-responders to biologic therapy than among responders opens the possibility that treatment with anti-PC could potentiate other treatments and also have a positive effect per se in RA, as well as cardiovascular diseases and cancer. Furthermore, our finding that the combination of high anti-PC levels with high anti-MDA-LDL levels and/or high anti-OxLDL levels in the ELSA study gave a strong protective effect against atherosclerosis suggests that a combination of these antibodies, as well as antibodies against components, fragments or derivatives of MDA-LDL or OxLDL (such as apoB100 or fragments thereof), would be more beneficial than single therapies. The antibodies could either be endogenously produced as a result of active immunization (vaccination), or exogenously administered (passive immunization). Likewise, our finding that a combination of low IgM anti-PC with low anti-OxCL or low anti-OxPS increases the excess risk of CVD would suggest that a combination of these antibodies could also improve therapy, if raised through active immunization or passive immunization.

The mechanism by which anti-TNF treatment was associated with increased anti-PC levels in the present study of patients with RA is not clear. One possibility is that TNF has a direct inhibitory effect on B cells producing anti-PC, but it is also possible that anti-PC are increased indirectly as a consequence of decreased inflammatory burden in general. Nevertheless, it is possible that a beneficial effect of anti-TNF treatment on IgM anti-PC may contribute to cardioprotective effects of this therapy.

While anti-TNF treatment has been extensively studied in the context of CVD, little is known about the risk of CVD associated with rituximab treatment in rheumatic diseases. Two small studies indicate that endothelial function may improve during such treatment[14,28].

In humans, treatment with rituximab induces an almost complete depletion of circulating B cells that usually lasts for 6 to 9 months, and in humans and primates persistent partial B-cell depletion may be found also in bone marrow and lymphoid organs[29]. Theoretically, depletion of B cells in autoimmune diseases should be limited to conventional B2 cells while sparing regulatory B10 cells and potentially protective B1 cells, the producers of natural antibodies[30], but that has not been proven in humans.

DETAILED SUMMARY OF THE INVENTION

One important finding herein is that rituximab treatment of RA patients was associated with a decrease in IgM anti-PC levels. At present, previous studies where this association has been reported in RA have not been conducted. However, other publications indicate that some, but not all, antibodies decrease after B-cell depleting therapy. For example, levels of serum IgG, IgA and antibacterial antibody levels remain relatively steady, whereas a single course of rituximab therapy leads to fall in titers of rheumatoid factor (RF), anti-citrullinated protein/peptide antibodies, anti-dsDNA and modest drops in serum IgM[21,31].

Accordingly, the present results could imply that treatment regimes with prolonged exposure of immune system to rituximab over time could cause increased long-term risk of CVD, even though it may ameliorate short-term negative effects of RA on CVD through its anti-inflammatory properties.

Both anti-TNF and rituximab treatment transiently worsened the oxLDL-status, which, however, returned to the baseline levels at the end of the study. To the best of our knowledge, possible changes of circulating oxLDL during therapy with biologics have not been examined earlier.

In RA, dyslipidemia combined with enhanced activity of pro-inflammatory cytokines leads to a pro-oxidative state, which further promotes oxidation of low-density lipoprotein (LDL) to the highly atherogenic oxidized LDL (oxLDL). OxLDL has also pro-inflammatory effects, such as activation of monocytes, endothelial cells, T cells and B cells[32]. The immunostimulatory and prothrombotic effects of oxLDL appear to be mediated through the platelet activating factor (PAF)-receptor, where phosphorylcholine (PC) is the major ligand[4]. Interestingly, oxLDL and foam cells are present in synovia in RA[33]. Several studies in the general population reported gradually increasing risk for CVD events with increasing plasma oxLDL[34,35].

A lot of attention has recently been focused on the apolipoproteins as CVD risk factors and important treatment target in the general population[36,37]. In contrast with some studies, but in line with others[38], we determined in both TNF and rituximab groups a beneficial increase in apoA1, already evident after 3 months of follow-up, which lasted during the one year of treatment without any distinct long-term change in atherogenic index. The fact that these changes occurred in both treatment groups suggests that the effect was not agent specific and an association with change of inflammatory activity was indeed found. It is thus possible that after longer treatment periods an improved lipoprotein profile may contribute to the decreased risk of CVD reported in RA patients on TNF-inhibition treatment[39]. Moreover, we noted interesting lipid changes in patients having the lowest apoA1 levels, the highest apoB levels, the highest atherogenic index or oxLDL levels. Thus, patients most susceptible to future cardiovascular events showed long-term improvement in apoA1, but at least short-term worsening in pro-atherogenic lipids without expected negative effect on atherogenic index.

In patients classified as responders according to the EULAR remission criteria, a transient moderate worsening in apoB and oxLDL without any obvious long-term worsening of lipid profile was observed. Whether these unfavorable and transient lipid changes could have some clinical importance is still not known. The inconsistency of the results in earlier reports regarding lipid changes during biologic therapy may arise from the fact that studies had different treatment durations, were conducted without consideration of the biologic efficacy and included heterogeneous patient populations.

The strength of the present study is in its prospective design, structured collection of blood samples and information about RA status at baseline, 3, 6 and 12 months of follow-up.

In summary, it is surprisingly found that levels of atheroprotective and anti-inflammatory anti-PC increased during anti-TNF treatment, but decreased in patients treated with rituximab. The results of the study extend beyond previous observations that apoA1 improves, but atherogenic index remains stable, during long-term biologic treatment.

Based on the present invention, it is further surprisingly shown that the level of anti-PC is lower among non-responders to biologic agents in therapy of RA than among responders.

Thus, this invention relates to anti-PC that can play a role as a risk marker and in the treatment of rheumatoid arthritis, other rheumatic, autoimmune, chronic inflammatory, cardiovascular and cancer diseases.

The invention further relates to the use of low anti-PC levels as a risk marker, and high levels as a protective marker, so individuals at risk could be identified and be eligible for treatment with anti-PC.

Even further, the invention also relates to the use of anti-PC as a complement to other immunomodulatory RA treatments wherein biologics, such as TNF-inhibitors (and other cytokine-inhibitors) and/or rituximab or other biologics acting on immunocompetent cells, are used, e.g. as in the treatment of RA.

The present invention also relates to antibodies against PC, PC conjugates and/or bioactive components and/or fragments thereof for use in combination and/or in combination therapy with biologic agents, especially for treating, preventing, and/or reducing the risk of developing chronic inflammatory, autoimmune and cancer diseases. Thus, antibodies against PC, PC conjugates and/or bioactive components and/or fragments thereof can be used in combination with other immunomodulatory treatments, where biologics such as TNF-inhibitors (and other cytokine-inhibitors) and/or rituximab or other biologics acting on immunocompetent B cells are used.

Biologic agents according to the present invention are of biological origin and are used to diagnose or treat disease, and may include proteins, peptides, cytokines, hormones, nucleic acids, lipids, phospholipids, carbohydrates, genetic resources, cells, organisms or parts thereof, populations, or any other biotic component of ecosystems.

Even further, biologic agents according to the present invention include stem cells, antibodies and fragments thereof, vaccines, interleukins and other cytokines, and may exhibit inhibitory effect on cytokine activity. Cytokine activity may be inhibited on the level of cytokine production, cytokine release, cytokine binding to cytokine receptors, and/or cytokine receptor activity, amongst others.

In accordance with the present invention, the term "cytokine" means regulatory proteins or glycoproteins, secreted by white blood cells and various other cells in the mammalian organism in response to numerous stimuli, facilitating cell-to-cell communication. Cytokines regulate the intensity and duration of an immune response by stimulating or inhibiting the activation, proliferation and/or differentiation of various cells, and by regulating the secretion of antibodies and other cytokines. In accordance with this invention, the group of cytokines includes, but is not limited to, interleukins (IL) and chemokines, as well as cytokines known by common names, such as Interferons (IFN) and tumor necrosis factors (TNF).

Interleukins may be secreted by white blood cells, as well as various other cells, and include the following interleukins, without being limited hereto: IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24 and IL-25.

Chemokines are mainly presented on white blood cells, however, not restricted hereto. A non-exhaustive list of chemokines includes: IL-8, GCP-2 (granulocyte chemotactic protein 2), Gro-α (growth related oncogene α), Gro-β (growth related oncogene β), Gro-γ (growth related oncogene γ), NAP-2 (neutrophil activating protein), ENA-78 (epithelial-cell-derived neutrophil-activating chemokine), IP-10 (Interferon-inducible protein-10), Mig (monokine induced by interferone γ), I-TAC (Interferon-inducible T-cell alpha chemoattractant), SDF-1 (stromal cell-derived factor-1), PBSF (pre-B-cell growth stimulating factor), BCA-1 (B-lymphocyte chemoattractant 1), MIP-1 (macrophage inflammatory protein 1), RANTES (regulated upon activation, normal T-cell expressed and secreted), MIP-5 (macrophage inflammatory protein 5), MCP-1 (monocyte chemoattractant protein 1), MCP-2 (monocyte chemoattractant protein 2), MCP-3 (monocyte chemoattractant protein 3), MCP-4 (monocyte chemoattractant protein 4), Eotaxin, TARC (thymus- and activation-regulated chemokine), MIP-1α (macrophage inflammatory protein 1α), MIP-1β (macrophage inflammatory protein 1β), Exodus-1, ELC (Ebl1 ligand chemokine).

The term "white blood cells" means all blood cells which are not platelets or red blood cells (i.e. erythrocytes), and are not limited to lymphocytes, monocytes, macrophages, dendritic cells, neutrophils, eosinophils and basophils. Natural killer cells, B- and T cells are included in the list of lymphocytes. Furthermore, the T cells may be divided into subgroups, such as Th (helper) cells, CD8+ cytotoxic T cells, regulatory (suppressor) T cells and gamma delta T cells. The term leukocytes may be used as a synonym for "white blood cells".

Interferons in accordance with this invention are included in the following non-exhaustive list: INF α, INF α-2a, INF α-2b, INF β, INF γ.

Tumor necrosis factors in accordance with this invention include, but are not limited to, TNF α and TNF β.

In accordance with the present invention, the term "cytokine production" means the synthesis of the cytokine inside white blood cells or various other cells in the mammalian organism.

In accordance with the present invention, the term "cytokine release" means the process of translocation of the cytokine from the interior of the cell to the exterior; the term "secretion" may also be used in this regard.

In accordance with the invention, the term "cytokine binding to cytokine receptor" means the specific binding of cytokines to receptors on the membrane of the target cell. The cytokine may bind receptors on the membrane of the same cell (autocrine action), to a receptor on a target cell in close proximity (paracrine action) and/or to distant target cells presenting the cytokine receptor (endocrine action).

In accordance with the invention, the term "cytokine receptor activity" means the triggering of a signal-transduction pathway, upon binding of the cytokine to the cytokine receptor as defined above, that ultimately alters gene-expression in the target cell.

In a particular embodiment of the present invention, biologic agents may be selected from the group comprising TNF blockers, such as, but not limited to, etanercept, infliximab, adalimumab, certolizumab pegol, golimumab, interleukin 1 (IL-1) blockers, such as, but not limited to, anakinra, monoclonal antibodies against B cells, such as, but not limited to, rituximab, T-cell costimulation blockers, such as, but not limited to, abatacept, Interleukin 6 (IL-6) blockers, such as, but not limited to, tocilizumab, or other antibodies, such as, but not limited to, antibodies against oxidized phospholipids and/or oxidized lipoproteins and/or fragments or derivatives thereof, such as, but not limited to, antibodies against apoB100 and/or fragments or derivatives thereof, anti-MDA-LDL, anti-OxLDL, anti-oxCL or anti-oxPS. Since biologic agents, such as Rituximab, may inhibit natural antibodies like anti-PC, and also may have a favourable effect on chronic inflammatory diseases like RA and SLE, the role of B cells in these diseases is coming more and more in focus. Therefore, other B-cell inhibiting agents are also of interest according to the present invention if they cause decreases in anti-PC levels.

In accordance with the present invention, the term "mammal" means all known mammals, and in particular mice, rats, rabbits, dogs, cats, cattle, horses and humans.

In accordance with the present invention, the medicament may be administered by any suitable means known by the skilled person and be formulated with excipients and adjuvants normally employed for such medicaments and their corresponding formulations. In particular, the medicament may be intended for administration by injection, optionally together with any suitable excipients and adjuvants employed for such formulations. Alternatively, the medicament may be given in the form of a pill, tablet or capsule.

The medicament may be administered in a way so as to be compatible with the dosage formulation and in such amount as will be therapeutically effective and/or immunogenic.

In accordance with the present invention, any agent that is suitable for increasing the anti-PC response, in particular PC conjugates, PC or bioactive components and/or parts thereof, optionally in combination with any suitable adjuvants, is to be considered as part of this invention. Such PC-exposing compounds also include platelet activating factor (PAF), PAF-like lipids or lysophosphatidylcholine, which have pro-inflammatory effects where PC is an important mediator.

In accordance with the present invention, monoclonal, polyclonal or chimeric antibodies of isotype IgA, IgD, IgE, IgG, IgM, raised against PC, PC conjugate or bioactive components and/or parts/fragments thereof (e.g. where PC is a component, such as is the case in PAF or PAF-like lipids), refer to any monoclonal or polyclonal antibody produced by immunization of a suitable mammal, including, but not limited to, mouse, rabbit, goat, sheep, or horse.

In accordance with the present invention, the term "bodily fluid" means any natural bodily fluid or secretion of fluid including, but not limited to, plasma, serum, blood, urine, or saliva.

In accordance with the present invention, the term "combination therapy" means the individual or simultaneous administration of two or more medications to treat a single disease and/or diseases that may develop due to unwanted medical side-effects or lack of satisfactory positive pharmaceutical response from the administration of one of the medications, e.g. unwanted medical side-effects due to the administration of biologic agents to treat chronic inflammatory diseases, autoimmune disease and cancer diseases.

In accordance with the present invention, "chronic inflammatory diseases, autoimmune and cancer diseases" means any of—including, but not limited to—the following diseases: cardiovascular disease (CVD), such as atherosclerosis, atheromatous plaque rupture, myocardial infarction, acute coronary syndrome, stroke, transient ischemic attack (TIA), claudication, angina pectoris; diabetes mellitus type 1 and 2, Alzheimer's disease, dementia in general, rheumatic diseases, acute and/or chronic inflammatory conditions, rheumatoid arthritis, psoriasis, psoriatic arthritis, ankylosing spondylitis, Reiter's Syndrome, systemic lupus erythematosus, dermatomyositis, Sjogren's syndrome, multiple sclerosis, myasthenia gravis, encephalitis, inflammatory bowel disease, arthritis, idiopathic inflammatory myopathies (IIM), dermatomyositis (DM), polymyositis (PM), inclusion body myositis, spondylopathies, vasculitis (including Wegeners granulomatosus, Takayasu arteritis, temporal arteritis), polymyalgia rheumatica, bowel disease including Crohn's disease and colitis of different kinds, nephritis, asthma, or cancer diseases, such as, but not limited to, non-Hodgkin's lymphoma, colorectal cancer, head and neck cancer and breast cancer and/or other cancer diseases where immunomodulation is used as treatment.

Immunotherapy is normally defined within medicine as "treatment of disease by inducing, enhancing, or suppressing an immune response". Passive immunity can be achieved through the transfer of ready-made antibodies into the affected individual or mammal. Immunotherapies designed to elicit or amplify an immune response are normally termed "activation immunotherapies", and include, for example, immunization. Immunotherapies designed to reduce, suppress or more appropriately direct an existing immune response, as in cases of autoimmunity or allergy, are normally termed "suppression immunotherapies". The active agents of immunotherapy are collectively called "immunomodulators", and include a wide variety of natural, synthetic and recombinant substances, many of which are biological agents as defined above. Examples of immunomodulators include medicinal mushrooms and herbs, various plant and microorganism extracts, vaccines, adjuvants, hormones, various drugs, interleukins, interferons and other cytokines.

Further, a detailed description of antibodies against PC conjugate, PC or bioactive components and/or fragments can be found in WO10/003602 ('602). As described in the '602 application, a PC-conjugate is a PC moiety linked to a carrier, optionally via a spacer. The structural element PC may, or may not, comprise a derivative of PC. The carrier can be, for example, a protein, a carbohydrate, a lipid, a polymer, latex beads, or colloid metal. The PC-conjugate may for example be a protein-PC conjugate, such as a human serum albumin (HSA)-PC conjugate, a keyhole limpet hemocyanin (KLH)-PC conjugate or a bovine serum albumin (BSA)-PC conjugate. Examples of PC-conjugates and generation of anti-PC antibodies are, e.g., described in WO 2005/100405 and U.S. Pat. No. 5,455,032, the contents of which are hereby included by reference. Thus, based on this it is clear that monoclonal antibodies reactive against PC conjugate, anti-PC or bioactive components and/or fragments can be produced using any standard method known in the art. See for example Briles et al., 1982. J Exp Med 156, 1177-1185 or Spira et al., 1988. J. Immunology 140, 2675-2680. Other antibodies against a phosphorylcholine and/or its conjugate can be prepared using methods well known to those skilled in the art. For example, a sub-fraction with anti-PC activity of a human immunoglobulin preparation can be prepared as described below by affinity purification using a PC conjugate.

Further, intravenous immunoglobulin preparations (e.g., IGIV; Baxter and others) are highly purified preparations of IgG commercially available and are used in the treatment of patients who have no, or very low levels, of antibody production. Immunoglobulin preparations include those available from the following manufacturers: Baxter (US), e.g., Gammagard®, Isiven (Antimo Naples, Italy), Omrix (Tel-Hashomer, Israel), Miles (Biological Products Division, West Heaven, Conn.), Sclavo (Lucca, Italy), Sandoz (Novautis, Basel, Swizeriand), e.g., Sandoglobulin®, Biotest Diagnostic Corporation (Deville, N.J.). Examples of immunoglobulin preparations are GammagardS/D®, GammarIV®, Gaimnar-PIV®, Gammimune N®, Iveegam®, Panglobulin®, Polygam S/D®, Sandoglobulin®, Venoglobulin®. Immunoglobulin preparations typically contain some IgM as well as IgG. Trace amounts of IgM are present in Gammagard®. Pentaglobin (Biotest) is an enriched IgM preparation, which has been used for treatment of SARS. The subfraction with anti-PC activity may comprise both IgG and IgM, or may be selected to comprise mainly IgG (for example by starting with an IgG-rich preparation, such as Gammagard® and/or by selecting for IgG); or mainly IgM (for example by starting with an IgM-rich preparation such as Pentaglobin and/or by selecting for IgM).

Further, an antibody preparation with specificity to a PC conjugate binds to unconjugated PC and may also bind to PC present in PC-containing compounds, in which PC is exposed, for example in lysophosphatidylcholine (see for example, Kim et al., 2002 J Exp Med. 196, 655-65). Thus, an antibody preparation with specificity to a PC conjugate may also bind to lysophosphatidylcholine or other phospholipids or phospholipid-containing compounds as platelet activating factor (PAF) or PAF-like lipids which have PC as a major component.

An embodiment of the present invention is thus to use PC conjugates or PC or bioactive components and/or parts thereof for the preparation of a pharmaceutical composition to be used in a treatment, prophylaxis and/or prevention prior to treatment of a mammal with biologic agents curing autoimmune diseases, chronic inflammatory diseases, and cancerous diseases. The conjugate can be PC linked to a pharmaceutically acceptable protein, carbohydrate, or polymer. The pharmaceutical composition is preferably given by injection, but can in practice be administered by any suitable means that allows the PC conjugate to provoke an immune response in the subject to which it is administered. The proposed method of active immunization will modulate the titre of anti-PC antibodies, which in turn will have a positive effect on the development of autoimmune diseases, chronic inflammatory diseases, and cancerous diseases. Thus, active immunization may be used to increase the titre of anti-PC antibodies to a level that, when assessed by the methods of diagnosis according to the present application, would not be said to be "low" or indicative of an increased risk of development, or progression, of autoimmune diseases, chronic inflammatory diseases, and cancerous diseases. Thus, a method of active immunization according to the present invention may be used to increase anti-PC levels, such as IgM anti-PC levels, in an individual to a level that is greater than about 10, 15, 20, 25, 30, 35, 40, 45, 50, 55, 60, 65, 70, 75, or 80 U/ml when tested by the methods described above. Accordingly, the method of active immunization according to the present invention may be used to increase anti-PC levels to a level that is above the mean average, or above a particular percentile value determined with reference to the wider population, such as above the 5th, 10th, 20th or 25th percentile, such as to a level, wherein the odds ratio is below one, the p-value is <0.05 and the upper limit of the odd ratio confidence interval is less than one, indicating a statistically significant level of low risk.

Another embodiment of the invention concerns the use of an antibody preparation, for example a monoclonal antibody, recognizing PC conjugates or PC or bioactive components and/or parts thereof for the preparation of a pharmaceutical composition to be used in a treatment, prophylaxis and/or prevention prior to treatment of a mammal with biologic agents for curing autoimmune diseases, chronic inflammatory diseases, and cancerous diseases. The monoclonal antibody can be produced using methods known in the art. Other antibody preparations may be used, such as anti-PC enriched preparations obtained from intravenous immunoglobulin preparations, recombinantly produced anti-PC antibodies and/or other artificially created anti-PC antibody derivatives, as discussed above. Thus, passive immunization may be used to increase the titre of anti-PC antibodies in an individual to a level that, when assessed by the methods of diagnosis according to the present application, would not be said to be "low" or indicative of an increased risk of development, or progression, of autoimmune diseases, chronic inflammatory diseases, and cancerous diseases. Thus, a method of passive immunization according to the present invention may be used to increase anti-PC levels, such as IgM anti-PC levels, in an individual to a level that is greater than about 10, 15, 20, 25, 30, 35, 40, 45, 50, 55, 60, 65, 70, 75 or 85 U/ml when tested by the methods described above. Accordingly, the method of active immunization according to the present invention may be used to increase anti-PC levels to a level that is above the mean average, or above a particular percentile value determined with reference to the wider population, such as above the 5th, 10th, 20th or 25th percentile, such as to a level wherein the odds ratio is below one, the p-value is <0.05 and the upper limit of the odd ratio confidence interval is less than one, indicating a statistically significant level of low risk.

One embodiment of the invention relates to antibodies against PC, PC conjugate or bioactive components and/or fragments thereof for use in combination therapy with one or more biologic agents and/or stem cells in a mammal. The antibodies can be used for curing, treating, preventing, and/or reducing the risk of developing autoimmune diseases, chronic inflammatory diseases, or cancerous diseases in a mammal, and can be monoclonal, polyclonal or chimeric antibodies of isotype IgA, IgD, IgE, IgG, IgM, optionally in combination with any suitable excipients or adjuvants. In preferred embodiments, the biologic agents are selected from the group comprising tumor necrosis factor alpha (TNFa) blockers, such as, but not limited to, etanercept, infliximab, adalimumab, certolizumab pegol, golimumab, Interleukin 1 (IL-1) blockers, such as, but not limited to, anakinra, monoclonal antibodies against B cells, such as, but not limited to, rituximab, T cell costimulation blocker, such as, but not limited to, abatacept, Interleukin 6 (IL-6) blockers, such as, but not limited to, tocilizumab, or other antibodies, such as, but not limited to, antibodies against oxidized phospholipids and/or oxidized lipoproteins and/or fragments or derivatives thereof, such as, but not limited to, antibodies against apoB100 and/or fragments or derivatives thereof, anti-MDA-LDL, anti-OxLDL, anti-oxCL or anti-oxPS. In particularly preferred embodiments, the biologic agents comprise one or more of the antibodies anti-MDA-LDL, anti-OxLDL, anti-oxCL and anti-oxPS.

Another embodiment according to the invention relates to antibodies against PC, PC conjugate or bioactive components and/or fragments thereof for immunization, treating, preventing, and/or reducing the risk of developing autoimmune diseases, chronic inflammatory diseases, and cancerous diseases in a mammal, said mammal being in therapy with biologic agents.

Yet another embodiment according to the invention relates to compositions comprising antibodies against PC, PC conjugates or bioactive components and/or fragments thereof in combination with one or more biologic agents and/or stem cells, particularly for use as a medicament, especially for curing, treating, preventing, and/or reducing the risk of developing autoimmune diseases, chronic inflammatory diseases, or cancerous diseases in a mammal.

Yet another embodiment according to the invention relates to antibodies against PC, PC conjugates or bioactive components and/or fragments thereof, or compositions comprising them, for use in preventing the rupture of atheromatous plaques.

Yet another embodiment according to the invention relates to antibodies against PC, PC conjugates or bioactive components and/or fragments thereof, or compositions comprising them, for use in preventing or treating cancer.

Yet another embodiment according to the invention relates to PC conjugates, PC or bioactive components and/or parts/fragments thereof for use in activation immunotherapy prior to or in combination (combination therapy) with the treatment of a mammal with biologic agents and/or stem cells for curing, treating, preventing, and/or reducing the risk of developing autoimmune diseases, chronic inflammatory diseases, and cancer diseases. In preferred embodiments, the biologic agents are selected from the group comprising tumor necrosis factor alpha (TNFa) blockers, such as, but not limited to, etanercept, infliximab, adalimumab, certolizumab pegol, golimumab, Interleukin 1 (IL-1) blockers, such as, but not limited to, anakinra, monoclonal antibodies against B cells, such as, but not limited to, rituximab, T cell costimulation blocker, such as, but not limited to, abatacept, Interleukin 6 (IL-6) blockers, such as, but not limited to, tocilizumab, or other antibodies, such as, but not limited to, antibodies against oxidized phospholipids and/or oxidized lipoproteins and/or fragments or derivatives thereof, such as, but not limited to, antibodies against apoB100 and/or fragments or derivatives thereof, anti-MDA-LDL, anti-OxLDL, anti-oxCL or anti-oxPS. In particularly preferred embodiments, the biologic agents comprise one or more of the antibodies anti-MDA-LDL, anti-OxLDL, anti-oxCL and anti-oxPS.

Yet another embodiment according to the invention relates to PC conjugates, PC or bioactive components and/or parts/fragments thereof for use in preventing the rupture of atheromatous plaques.

Yet another embodiment according to the invention relates to PC conjugates, PC or bioactive components and/or parts/fragments thereof for use in preventing or treating cancer.

Yet another embodiment according to the invention relates to the use of antibodies against PC, PC conjugates or bioactive components and/or fragments thereof, or compositions comprising them, in preventing the rupture of atheromatous plaques.

Yet another embodiment according to the invention relates to the use of antibodies against PC, PC conjugates or bioactive components and/or fragments thereof, or compositions comprising them, in preventing or treating cancer.

Yet another embodiment according to the invention relates to the use of PC conjugates, PC or bioactive components and/or parts/fragments thereof in preventing the rupture of atheromatous plaques.

Yet another embodiment according to the invention relates to the use of PC conjugates, PC or bioactive components and/or parts/fragments thereof in preventing or treating cancer.

A further embodiment according to the invention relates to a composition comprising phosphorylcholine (PC), PC conjugate and/or bioactive components and/or fragments thereof in combination with biologic agents. In preferred embodiments, the biologic agents are selected from the group comprising tumor necrosis factor alpha (TNFa) blockers, such as, but not limited to, etanercept, infliximab, adalimumab, certolizumab pegol, golimumab, Interleukin 1 (IL-1) blockers, such as, but not limited to, anakinra, monoclonal antibodies against B cells, such as, but not limited to, rituximab, T cell costimulation blocker, such as, but not limited to, abatacept, Interleukin 6 (IL-6) blockers, such as, but not limited to, tocilizumab, or other antibodies, such as, but not limited to, antibodies against oxidized phospholipids and/or oxidized lipoproteins and/or fragments or derivatives thereof, such as, but not limited to, antibodies against apoB100 and/or fragments or derivatives thereof, anti-MDA-LDL, anti-OxLDL, anti-oxCL or anti-oxPS. In particularly preferred embodiments, the biologic agents comprise one or more of the antibodies anti-MDA-LDL, anti-OxLDL, anti-oxCL and anti-oxPS.

Experimental

The materials and methods and examples disclosed below are provided only for the purpose of illustrating the present invention and should not be considered as any limitation of the scope as outlined in the appended claims.

Patients and Methods

Patients

In all, 215 outpatients with RA (ACR criteria 1987)[40] were identified from a prospective cohort of RA patients registered in the local database including all patients treated with biologics at the Rheumatology Department, Karolinska University Hospital Huddinge. They started their treatment with anti-TNF (etanercept, infliximab and adalimumab) or rituximab between January 2000 and October 2007 and were included consecutively in this study in case they had been treated for at least one year, moreover, in case of TNF-treatment, if they had been biologic-naive earlier. At this time, Rituximab was used mainly in patients that had failed on anti-TNF-therapy, and thus, 68% of these patients had got anti-TNF treatment earlier. Rituximab was the first biologic in case of history of recurrent infections, lymphoma, lung fibrosis or family history of multiple sclerosis. Concomitant disease-modifying antirheumatic drugs (DMARD) were chosen by the treating physicians in accordance with the current recommended treatment strategy in Sweden.

Assessments of disease activity had been done at treatment initiation and after 3, 6 and 12 months. These included the composite disease activity score DAS28[41], CRP, ESR and the modified version of Stanford Health Assessment Questionnaire, HAQ[42].

In addition, from medical records information was obtained on RA disease characteristics, traditional CVD risk factors (current and previous smoking, hypertension and diabetes mellitus), history of CVD (myocardial infarction, congestive heart failure, angina pectoris and stroke), medications and also blood pressure and body mass index (BMI). Current hypertension was defined as a blood pressure above 140/90 mmHg or being treated with anti-hypertensive drugs.

The study was approved by the Ethics committee at Karolinska Institute, Stockholm, Sweden, reference number 2008/159-31, and was performed in accordance with the Helsinki declaration.

Serum Analyses

Sera were obtained at baseline, and at 3, 6 and 12 months of follow-up, and stored at −70° C. until all samples were analyzed. Anti-PC IgM and oxLDL were determined by ELISA (Athera Biotechnologies AB, Stockholm, Sweden and Mercodia AB, Uppsala, Sweden, respectively) according to the protocols provided by the manufacturers and essentially as described earlier[17,43]. Apolipoproteins A1 (ApoA1) and B (ApoB) were determined by an immunoturbidimetry (Modular Analytics P, Roche Diagnostics).

Statistical Analysis

Clinical characteristics were compared between groups using Kruskal-Wallis test for multiple samples or Mann-Whitney U test for two samples for continuous variables, chi-square test or Fisher's exact test for dichotomous variables. We employed McNemar's test for dichotomous outcomes in analysis of differences in one sample at different time-points. The association between baseline level of antibodies and progression of clinical characteristics was determined using Spearman rank correlation. To analyze changes in IgM anti-PC, oxLDL, apolipoprotein levels and influence of independent covariates on primary outcomes we used linear mixed model with correction for random effects in the complete longitudinal dataset, the assumptions for analysis were valid. Log transformations were undertaken if needed in order to obtain normality of variable distributions. Level of significance was chosen to be $\alpha<0.05$. Calculations were performed using STATISTCA, release 8 (Stat Soft Scandinavia AB, Tulsa, Okla., USA).

DAS stands for "Disease Activity Score" and is a measure of the activity of rheumatoid arthritis. In Europe, the DAS method is the recognized standard in research and clinical practice and a well-known terminology ordinary to the skilled person.

BRIEF DESCRIPTION OF THE DRAWINGS

FIG. 2. Panel A and B represent anti-PC changes in responders vs. non-responders as to remission (DAS28<2.6) in anti-TNF total and rituximab groups under the follow-up. Original data log transformed, adjusted (sex and age) LS means where vertical bars denote 0.95 confidence intervals. Post-hoc test (pooled MSE, between and within effects considered) was used for comparisons at different time points. DAS28=disease activity score calculated on 28 joints.

EXAMPLE 1

Figure 1:
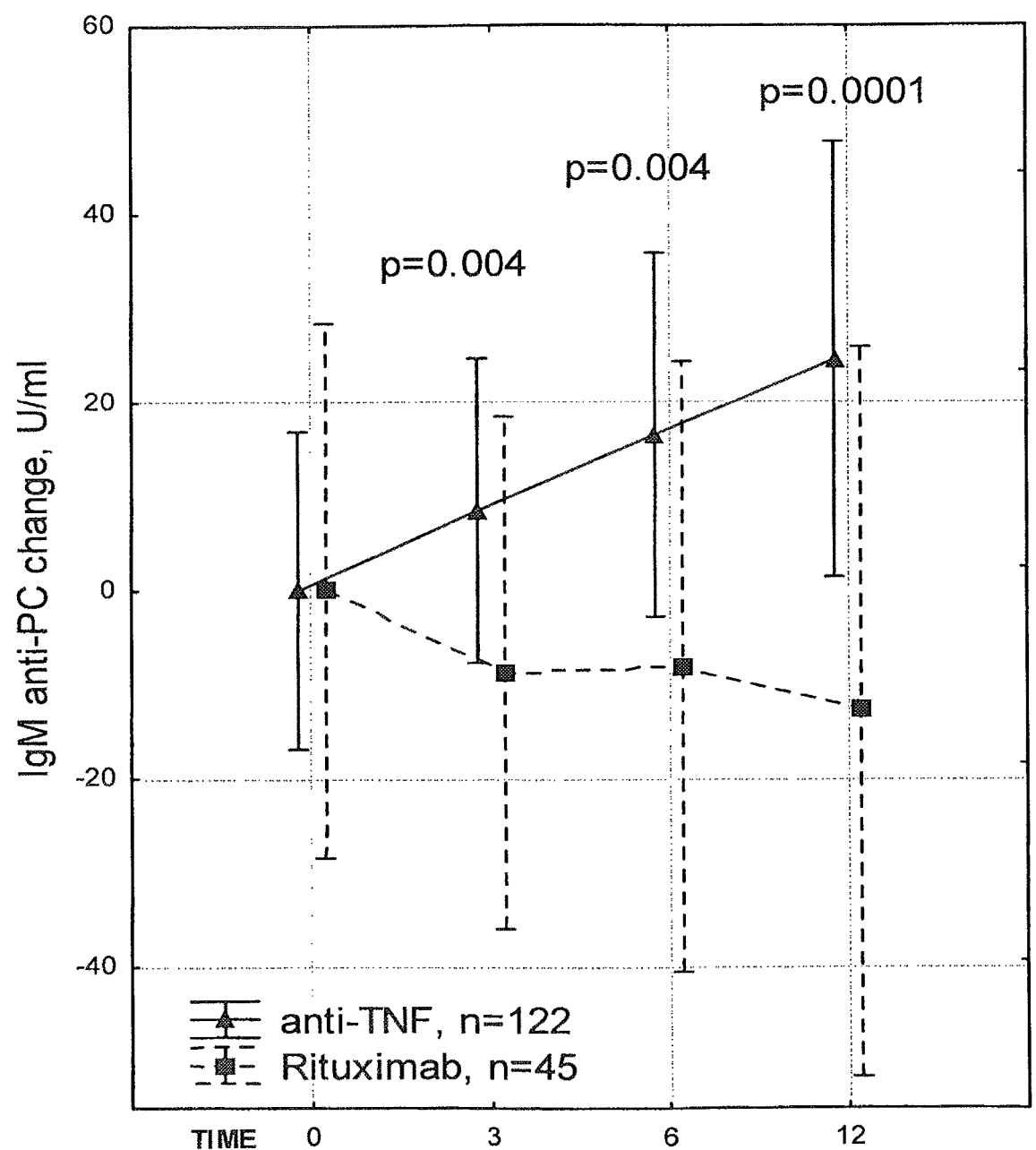
FIG. 1. Changes of IgM anti-PC levels from baseline over 3, 6 and 12 months of follow-up in the anti-TNF total and Rituximab groups. Adjusted (sex, age, smoking habits) LS means are shown, where the vertical bars denote 0.95 confidence intervals. Post-hoc test (pooled MSE, between and within effects considered) was used for comparisons at different time points.

Effects of Biologic Agents on Levels of Antibodies Against Phosphorylcholine

Results

Demographic and clinical characteristics of the patients studied are summarized in Table 1.

The characteristics were similar for the etanercept, infliximab and adalimumab patients, apart from a lower proportion of current hypertension in patients offered etanercept and a higher proportion of concomitant use of methotrexate (MTX) among patients starting infliximab, the latter in conformity to treatment recommendation.

Patients started on Rituximab were older, had longer disease duration, higher frequency of RF-positivity and occurrence of erosive joint disease than the anti-TNF treated patients. These patients were less commonly treated with MTX but instead more often with other DMARDs (azathioprine, sulfasalazine, leflunomide, cyclosporine, gold) and with glucocorticoids (GC). Furthermore, they were more often previous smokers, had higher frequency of CVD comorbidity and treatment with statins.

In all treatment groups, history of hypertension was relatively frequent and mean BMI close to borderline for overweight (BMI>25 kg/m$^2$), with no statistical differences between treatment groups.

Disease Activity and Function

All patients had high disease activity at baseline measured by DAS28, CRP and ESR and low functional capacity measured by HAQ, with no intergroup difference for the anti-TNF agents. However, patients started on Rituximab had significantly higher DAS28 and HAQ-score than the anti-TNF treated groups, table 1.

Already at the 3-month follow-up, about ⅔ of the patients in all treatment groups experienced significant improvement according to DAS28; thus, mean±SD DAS28 in the total TNF-group vs. the Rituximab group was 3.9±1.2 and 4.2±1.3, respectively. This positive effect was present during the whole follow-up period, reaching a mean±SD DAS28 3.7±1.5 vs. 4.5±1.6 at the end of the study. At both the 3 and 12 month follow-ups, patients on anti-TNF treatment had significantly lower DAS28 than the Rituximab treated patients, p=0.026 and p=0.002 respectively, with no intra group difference. However, the change in DAS28 throughout the study period did not differ significantly between anti-TNF and anti-B-cell treated subjects, p=0.108.

Physical ability improved during follow-up as well; thus, HAQ-score at 12 months had decreased, mean±SD, 0.3±0.5 in anti-TNF treated patients and with 0.2±0.4 in Rituximab-treated subjects, without significant intra group differences for TNF-α treatments or difference between anti-TNF vs. rituximab group, p=0.618 and p=0.118 respectively.

Concomitant Treatment

The DMARD therapy was fairly constant during the study period. The GC treatment could be stopped in low percentages of the patients and similarly in all treatment groups. At the 12-month visit, the Rituximab group was still significantly more often treated with GC, 73.6% vs. 27.2% for the anti-TNF treated groups, p<0.0001. However, the daily GC dosage had been decreased more in the Rituximab group at the 12-month of follow-up, at which time the intergroup difference had disappeared. In all groups the use of NSAID diminished during the study period. Treatments against hypertension and hyperlipidemia were unchanged during the study period.

Levels of Antibodies Against Phosphorylcholine (Anti-PC) of IgM Subclass

At baseline, anti-PC levels were higher in the etanercept and lower in the adalimumab-treated subjects compared with the infliximab and rituximab groups, p=0.001. There was no statistically significant difference in baseline anti-PC between the TNF group total vs. the rituximab group, p=0.444.

In the whole anti-TNF group, anti-PC had increased significantly already after 3 months of therapy, and a further increase was evident at both 6 and 12 months, table 2. In the separate anti-TNF groups, there was a trend towards increasing antibody levels after 3 months of treatment in all three groups, reaching statistical significance at 12 months in patients on etanercept and infliximab therapy, but not on adalimumab (a high percentage of missing data at 6 and 12 months of follow-up, 33 an 23% respectively, was noted in this group). In contrast to anti-TNF treatment, in patients receiving rituximab there was a statistically significant decrease in anti-PC levels at 12 months, table 2.

At all time-points of follow up, the anti-PC levels were significantly higher in total anti-TNF group vs. Rituximab-treated group as presented in FIG. 1 (adjusted for sex, age and smoking habits). The curve illustrating anti-PC increase in the total anti-TNF group contrasts with those of B cells therapy where a continuous declining trend was noted. The overall treatment effect on antibody levels was strikingly evident with high statistical significance (p<0.0001). Thus, beneficial effects on IgM anti-PC on TNF-blockade, but disadvantageous effects on rituximab were observed during the 12 months' study period.

A large between and within individual variation in antibody levels was consistently noticed in all treatment groups throughout the study period, with positive covariance of mild-grade 0.55-0.73 for subjects having TNF-α treatment and of low-grade 0.11-0.26 for the Rituximab group.

Subgroup analysis revealed that anti-PC levels at baseline were significantly lower in male compared with female, median (IQR) 37.8 (26.88-65.78) vs. 55.63 (33.13-96.70) U/ml, p=0.007. Analysis restricted to subgroups of TNF-treated patients revealed that there was a tendency towards a more prominent increase in antibody levels in females and in middle-aged patients without a history of smoking (data not shown). This gender discrepancy may be one explanation why the increasing levels of anti-PC levels in subjects offered adalimumab (with a higher frequency of males compared with the two other anti-TNF groups) did not reach statistical significance. We did not find significant influence of any baseline variables on anti-PC decrease in the rituximab treated subjects.

Association Between IgM Anti-PC Levels and Disease Activity

There were no significant correlations between anti-PC concentration at the beginning of treatment and initial levels of the inflammatory markers CRP, ESR, DAS28 or with lipid profile measured as apoA1, apoB and apoB/apoA1 ratio.

In the anti-TNF total group, baseline levels of anti-PC differed in subjects responding vs. those not responding to treatment. Thus, patients achieving remission at 12 months, DAS28<2.6, on anti-TNF treatment had significantly higher baseline anti-PC levels than those not in remission, p=0.007, and this difference in anti-PC levels was present at all follow-up time-points (FIG. 2A). Also in patients on rituximab, baseline anti-PC levels were higher in those who later achieved remission, p=0.041 (FIG. 2B).

For the anti-TNF total group, there were negative correlations between absolute change (Δ) in anti-PC with changes in both clinical activity and physical ability from baseline to 12 months of follow-up as follows: r=−0.17, p=0.033 for ΔCRP; r=−0.21, p=0.010 for ΔESR; r=−0.18, p=0.029 for ΔDAS28; r=−0.17, p=0.05 for ΔHAQ. Relative changes in anti-PC correlated quite well with absolute changes of clinical characteristics. Thus, the change in anti-PC level was associated with overall decrease of inflammation in patients on anti-TNF treatment. In the rituximab group there was no evident relation between anti-PC and clinical variables.

Levels of oxLDL and Apolipoproteins

OxLDL levels at baseline differed significantly between the anti-TNF groups but not between the anti-TNF total vs. the rituximab group. The oxLDL levels were shown to be lower with increasing age, the age-depended oxLDL difference showed statistical significance, p=0.002, (age categorized <45, 45-65 and >65 years old). No difference in oxLDL level was detected in regard to other patients' characteristics.

Baseline concentrations of apoA1, apoB and apoB/apoA1 ratio did not differ statistically between the treatment groups (Table 3). Mean apoA1 was normal, >1.29 g/l, but a proatherogenic profile was shown for apoB and apoB/apoA1 ratio; thus, mean apoB was >0.88 g/l and mean apoB/apo1 ratio was >0.69 in all study subgroups.

OxLDL had increased significantly at 3 months of therapy on adalimumab, anti-TNF total and on rituximab treatments, but this increase waned thereafter to almost initial levels (Table 3).

ApoA1 levels increased somewhat on the various therapies—at 3 months in the total anti-TNF group, at 6 months in the total anti-TNF and in the rutuximab group, and towards 12 months apoA1 stabilized but maintained still higher levels than at baseline. Thus, at the end of follow-up apoA1 had increased, on average, by 8.5% on etanercept, by 2.3% in the anti-TNF total and by 6.7% on rituximab, with no significant intergroup difference.

The atherogenic ratio, apoB/apoA1, and apoB did not change significantly over time and remained relatively stable throughout the whole study period, except for the adalimumab treatment group where a small rise in apoB was detected after 3 months of follow-up, this increase disappeared and apoB levels reverted to initial levels after 6 months of therapy.

Previous population-based studies suggest that apolipoproteins are useful predictors of risks for CVD. However, cut-off levels for apolipoproteins in RA population are not established. With regard to possible CVD risks, we performed analysis after tertiary subdividing of initial blood lipids. Data was dichotomized according to the 33% percentile for apoA1 and the 66% percentile for oxLDL, apoB and apoB/apoA1. Because of small sample sizes, analyses were limited to the anti-TNF total vs. the rituximab-treated groups (Table 4).

The biologic treatments resulted in an initial increase in percentage of subjects with high oxLDL and apoB, which was followed by a beneficial decrease to approximately initial levels at 12 months in patients on anti-TNF, but remained still high in patients on rituximab. On rituximab, the percentage of subjects with elevated apoB, despite more frequent use of statins, was statistically higher than in the anti-TNF total group at 6 months of follow-up, p=0.042.

The frequency of subjects with low apoA1 in the anti-TNF group decreased at 3-6 months of follow-up and then increased towards 12 months, but was then still lower than at the treatment initiation. In the rituximab group, the frequency of patients with low apoA1 was consistently decreasing throughout the whole study period. There was no between-group difference.

Seemingly, as shown in table 4, the TNF-blockade in comparison with rituximab induced opposite effects on apoB/apoA1 ratios at 3-6 months of follow-up, but no statistically significant between-group difference was observed. Anyway, a slightly lower percentage of subjects with elevated atherogenic index was shown at 12 months in both groups.

Thus, both anti-TNF and rituximab treatments caused short-term improvement in the lowest apoA1 tertile but transient increases of apoB and oxLDL levels in the highest tertile without unequivocal influences on atherogenic index during one year of the study period. Besides, the results suggest that TNF-a blockade and B cells therapy may have different effects on lipid profile.

Association Between Lipid Levels and Disease Activity

Associations between lipid changes and changes in inflammatory markers during the period of follow-up were similar in the patients on TNF-blockade and rituximab. In the whole study population, absolute change ($\Delta$) in oxLDL levels were inversely correlated with $\Delta$CRP at 3 months, r=−0.18, p=0.009; at 6 months, r=−0.26, p=0.001, and at 12 months, r=−0.24, p=0.001. In the same way, a low-moderate negative association was observed between $\Delta$apoA1 and $\Delta$CRP at 3 months, r=−0.17, p=0.108, at 6 months, r=−0.23, p=0.002, and at 12 months, r=−0.27, p=0.0001. We did not detect any obvious associations between apoB, apoB/apoA1 ratio and changes in disease activity.

In order to investigate if the lipid changes varied according to clinical response, we performed sub-analysis (sex and age adjusted) according to EULAR remission criteria DAS28<2.6 at 12 months in the anti-TNF total and the rituximab groups.

At baseline, 3 and 12 months there were no significant differences in studied lipid levels between responders and non-responders, neither in the anti-TNF total group nor in the rituximab group, with exception of apoB, where responders had lower initial apoB level, on average 14.3%, p=0.037.

At 6 months, however, lipid levels were significantly, but still moderately, lower among responders in regard to levels of oxLDL, 7%, p=0.003 on anti-TNF and 7%, p=0.017 on Rituximab treatment; and in regard to levels of apoA1, on average 16.1%, p=0.004; apoB, 12.1%, p=0.005 on anti-TNF therapy. There was no difference in the atherogenic index between responders and non-responders.

Thus, a temporary difference in oxLDL, apoA1 and apoB in patients on TNF-blockade and in oxLDL in patients on rituximab was registered between subjects achieving clinical remission and those not achieving it after one year of biologic therapy.

TABLE 1

Baseline demographic and clinical characteristics of the RA patients, by treatment group

|  | Etanercept n = 60 | Infliximab n = 60 | Adalimumab n = 42 | $p^1$-value | TNF-a total n = 162 | Rituximab n = 53 | $p^2$-value |
| --- | --- | --- | --- | --- | --- | --- | --- |
| Age, yrs | 54.6 ± 12.5 | 56.6 ± 12.2 | 57.9 ± 12.7 | 0.38 | 56.2 ± 12.4 | 63.3 ± 10.7 | 0.0001 |
| Age, RA-onset, yrs | 43.7 ± 13.5 | 46.1 ± 12.8 | 47.4 ± 14.6 | 0.43 | 45.6 ± 13.5 | 49.4 ± 11.6 | 0.045 |
| Female, n (%) | 47 (78.3) | 43 (71.7) | 27 (64.3) | 0.29 | 117 (72.2) | 45 (84.9) | 0.06 |
| Duration of RA, yrs | 7.5 (5-14) | 9 (4-15) | 5 (3-11) | 0.34 | 7 (4-14) | 11 (7-17) | 0.003 |
| RF-positivity, n (%) | 51 (85.0) | 51 (85.0) | 30 (71.4) | 0.15 | 132 (81.5) | 52 (98.1) | 0.003 |
| Erosive disease, n (%) | 54 (90.0) | 52 (86.7) | 31 (73.8) | 0.07 | 137 (84.6) | 51 (96.2) | 0.026 |
| Current smoker, n (%) | 14 (23.3) | 16 (26.7) | 9 (21.4) | 0.69 | 39 (24.1) | 9 (17.0) | 0.32 |
| Previous smoker, n (%) | 4 (6.0) | 9 (15.0) | 9 (21.4) | 0.12 | 22 (13.6) | 18 (34.0) | 0.035 |
| CVD comorbidity, n (%) | 14 (23.3) | 20 (33.3) | 12 (28.6) | 0.48 | 46 (28.4) | 25 (47.2) | 0.012 |
| History of hypertension, n (%) | 13 (21.7) | 17 (28.3) | 12 (28.6) | 0.64 | 42 (25.9) | 19 (35.9) | 0.16 |
| Current hypertension, n (%) | 27 (48.2) | 40 (69.0) | 23 (69.7) | 0.040 | 90 (61.2) | 32 (60.4) | 0.91 |
| Current diabetes mellitus, n (%) | 2 (3.3) | 6 (10.0) | 1 (2.4) | 0.06 | 9 (5.6) | 7 (13.2) | 0.07 |
| Statin use, n (%) | 3 (5.0) | 2 (3.3) | 1 (2.4) | 0.80 | 6 (3.7) | 6 (11.3) | 0.040 |
| BMI, kg/m$^2$ | 24.2 ± 4.4 | 25.3 ± 3.9 | 25.9 ± 5.2 | 0.30 | 25.2 ± 4.6 | 25.9 ± 4.5 | 0.33 |
| CRP, mg/l | 25 (10-42) | 23 (10-38) | 15 (9-58) | 0.64 | 22 (10-41) | 28 (14-57) | 0.11 |
| ESR, mm/hr | 39 (27-49) | 34 (27-55) | 35.5 (19-64) | 0.912 | 41.2 ± 24.0 | 36 (28-65) | 0.25 |
| DAS28 | 5.6 ± 0.9 | 5.7 ± 1.0 | 5.6 ± 1.3 | 0.857 | 5.7 ± 1.0 | 6.1 (±1.1) | 0.010 |
| HAQ-score | 1.2 ± 0.7 | 1.4 ± 0.6 | 1.4 ± 0.6 | 0.219 | 1.3 ± 0.6 | 1.5 ± 0.5 | 0.033 |
| DMARD use: |  |  |  |  |  |  |  |
| MTX, n (%) | 38 (63.3) | 58 (96.7) | 30 (71.4) | <0.0001 | 126 (77.8) | 23 (43.4) | <0.0001 |
| Other DMARDs n (%) | 9 (15.0) | 10 (16.7) | 6 (14.3) | 0.94 | 25 (15.4) | 22 (41.5) | 0.0001 |
| GC use, n (%) | 19 (31.7) | 18 (30.0) | 17 (40.5) | 0.51 | 54 (33.3) | 42 (79.3) | <0.0001 |

TABLE 1-continued

Baseline demographic and clinical characteristics of the RA patients, by treatment group

| | Etanercept n = 60 | Infliximab n = 60 | Adalimumab n = 42 | p¹-value | TNF-a total n = 162 | Rituximab n = 53 | p²-value |
|---|---|---|---|---|---|---|---|
| GC, mg/day | 5.5 ± 1.6 | 5.0 (5-7.5) | 7.5 (5-8.8) | 0.15 | 5 (5-7.5) | 7.5 (5-15) | 0.0001 |
| NSAID, n (%) | 44 (73.3) | 42 (70.0) | 26 (61.9) | 0.462 | 112 (69.1) | 31 (58.5) | 0.154 |

Except where indicated otherwise, values are denoted as mean ± SD or median (IQR) depending on values distribution.

p¹ indicates p-value for differences between the three TNF-a offered treatment groups, p² for differences between TNF-a total and B cells therapy groups. Bold p-values are statistically significant. CVD = cardiovascular disease, BMI = body mass index, DAS28 = disease activity score for 28 joints, HAQ = health assessment questionnaire, DMARD = disease modifying anti-rheumatic drug, GC = glucocorticoid, NSAID = non-steroidal anti-inflammatory drug, yrs = years.

TABLE 2

Antibody levels of IgM subclass against phosphorylcholine (anti-PC) at baseline and changes at the follow-up time-points, by treatment group

| anti-PC, U/ml | Etanercept n = 60 | Infliximab n = 60 | Adalimumab n = 42 | Anti-TNF total n = 162 | Rituximab n = 53 |
|---|---|---|---|---|---|
| baseline | 67.61 (46.4-115.8) | 41.59 (33.6-88.5) | 36.59 (24.3-64.6) | 51.61 (32.9-94.5) | 42.88 (31.6-81.5) |
| Δ 3-0 | 6.87 (−4.54; 26.83) | 2.56 (−6.23; 11.98) | 0.07 (−1.91; 8.56) | 2.25 (−4.03; 13.24) | −5.2 (−10.69; −1.64) |
| p-value | 0.15 | >0.5 | >0.5 | 0.012 | 0.35 |
| Δ 6-0 | 4.99 (−3.86; 34.73) | 6.46 (−2; 12.3) | −0.85 (−4.08; 7.1) | 3.92 (−3.63; 19.6) | −6.11 (−11.35; −0.35) |
| p-value | 0.28 | >0.5 | >0.5 | 0.001 | >0.5 |
| Δ 12-0 | 8.67 (−5.82; 42.6) | 8.47 (−2.05; 19.14) | 4.73 (−1.99; 15.23) | 8.27 (−2.38; 27.92) | −8.02 (−15.28; −1.14) |
| p-value | 0.002 | 0.046 | >0.5 | <0.0001 | 0.023 |

Results are indicated as median (IQR). Δ = changes; 3-0, 6-0 and 12-0 concern differences between respective periods of follow-up, 3, 6 and 12 months and 0 = baseline.
p-values are given for changes in anti-PC between the respective time-points and are marked in bold if statistically significant.
The number of patients was in the etanercept group 60 at all time-points; in the infliximab group 60 at baseline, 58 at 3 months, 48 at 6 months and 58 at 12 months; in the adalimumab group 42 at baseline, 42 at 3 months, 28 at 6 months and 32 at 12 months; and for the rituximab group 53 at baseline, 50 at 3 months, 52 at 6 months and 48 at 12 months.

TABLE 3

Lipid levels at baseline and changes at the follow-up time-points, by treatment group

| Lipids | Etanercept | Infliximab | Adalimumab | Anti-TNF total | Rituximab |
|---|---|---|---|---|---|
| oxLDL, U/l | | | | | |
| Baseline | 74 (56.8-95.1) | 67.26 ± 19.7 | 57.86 ± 20.32 | 64.7 (51.9-83.8) | 61.18 ± 17.47 |
| Δ 3-0 | 0.14 ± 27.3 p = 0.75 | 2.48 ± 12.77 p = 0.10 | 5.85 ± 13.44 p = 0.004 | 2.49 ± 19.66 p = 0.011 | 3.67 ± 12.18 p = 0.023 |
| Δ 6-0 | 1.39 ± 28.47 p = 0.54 | 1.3 (−6.8; 11.2) p = 0.26 | 0.33 ± 19.01 p = 0.88 | 2.05 ± 22.88 p = 0.20 | 2.75 ± 11.95 p = 0.10 |
| Δ 12-0 | 1.79 ± 29.4 p = 0.39 | −0.24 ± 13.98 p = 0.80 | 2.9 (−5.3; 12.4) p = 0.35 | 0.55 ± 22.10 p = 0.31 | 2.37 ± 14.26 p = 0.31 |
| ApoA1, g/l | | | | | |
| Baseline | 1.29 ± 0.31 | 1.34 ± 0.30 | 1.28 ± 0.29 | 1.31 ± 0.28 | 1.34 ± 0.28 |
| Δ 3-0 | 0.03 (−0.16; 0.2) p = 0.70 | 0.05 ± 0.31 p = 0.11 | 0.10 ± 0.31 p = 0.017 | 0.04 ± 0.32 p = 0.013 | 0.03 ± 0.25 p = 0.30 |
| Δ 6-0 | 0.03 (−0.07; 0.16) p = 0.037 | 0.06 (−0.07; 0.2) p = 0.23 | 0.02 ± 0.39 p = 0.31 | 0.07 (−0.08; 0.19) p = 0.012 | 0.09 ± 0.32 p = 0.022 |
| Δ 12-0 | 0.11 ± 0.22 p = 0.0001 | 0.03 (−0.18; 0.16) p = 0.87 | 0.01 ± 0.47 p = 0.53 | 0.03 ± 0.36 p = 0.007 | 0.09 ± 0.32 p = 0.06 |

TABLE 3-continued

Lipid levels at baseline and changes at the follow-up time-points, by treatment group

| Lipids | Etanercept | Infliximab | Adalimumab | Anti-TNF total | Rituximab |
|---|---|---|---|---|---|
| ApoB, g/l | | | | | |
| Baseline | 0.88 ± 0.22 | 0.90 ± 0.28 | 0.92 ± 0.28 | 0.90 ± 0.26 | 0.95 ± 0.25 |
| Δ 3-0 | −0.04 ± 0.23 | 0.05 ± 0.22 | 0.07 ± 0.20 | 0.02 ± 0.22 | 0 ± 0.18 |
| | p = 0.46 | p = 0.09 | p = 0.042 | p = 0.11 | p = 0.97 |
| Δ 6-0 | 0 (−0.09; 0.11) | −0.01 ± 0.21 | −0.06 ± 0.23 | −0.02 ± 0.21 | 0.03 ± 0.18 |
| | p = 0.77 | p = 0.80 | p = 0.20 | p = 0.51 | p = 0.19 |
| Δ 12-0 | 0.04 ± 0.17 | −0.01 ± 0.25 | −0.05 (−0.2; 0.15) | 0.03 (−0.11; 0.13) | 0.03 ± 0.22 |
| | p = 0.12 | p = 0.78 | p = 0.48 | p = 0.47 | p = 0.67 |
| B/A1 ratio | | | | | |
| Baseline | 0.70 ± 0.21 | 0.70 ± 0.24 | 0.74 ± 0.25 | 0.71 ± 0.23 | 0.68 (0.61-0.85) |
| Δ 3-0 | −0.02 ± 0.15 | 0.01 ± 0.17 | 0.02 ± 0.18 | 0.003 ± 0.16 | −0.01 ± 0.14 |
| | p = 0.50 | p = 0.60 | p = 0.64 | p = 0.95 | p = 0.78 |
| Δ 6-0 | −0.02 ± 0.13 | −0.03 (−0.11; 0.08) | −0.05 ± 0.20 | −0.03 (−0.11; 0.07) | −0.02 ± 0.15 |
| | p = 0.37 | p = 0.45 | p = 0.23 | p = 0.11 | p = 0.56 |
| Δ 12-0 | −0.03 ± 0.11 | 0.02 ± 0.19 | −0.06 ± 0.20 | −0.02 ± 0.17 | −0.02 ± 0.17 |
| | p = 0.12 | p = 0.57 | p = 0.22 | p = 0.31 | p = 0.25 |

Results are indicated as mean ± SD or median (IQR) depending on values distribution. Δ = changes; 3-0, 6-0 and 12-0 concern differences between respective periods of follow-up, 3, 6 and 12 months and 0 = baseline, the number of patients as indicated in table 2.
p-values are given for changes in the lipids between the respective time-points and are marked in bold if statistically significant. There were no significant group differences between total anti-TNF vs. rituximab treatment. OxLDL = oxidized low-density lipoprotein, apoA1 = apolipoprotein A1, apoB = apolipoprotein B, B/A1 = apoB/apoA1.

TABLE 4

Changes in patient percentages above the 66% percentile of oxLDL, apoB and apoB/apoA1 and below the 33% percentile of apoA1, respectively, during the study, by treatment groups

| | Anti-TNF total | Rituximab | $p^4$-value |
|---|---|---|---|
| OxLDL | | | |
| 66 percentile U/l baseline, % [CI] | >76.5<br>33.3 [26.1; 40.6] | >65.2<br>33.9 [21.2; 46.7] | |
| 3 months, % [CI]<br>$p^1$-value | 37.5 [30.0; 45.0]<br>0.0003 | 38.0 [24.6; 51.5]<br>0.029 | 0.95 |
| 6 months, % [CI]<br>$p^2$-value | 38.2 [30.1; 46.4]<br><0.0001 | 44.2 [30.7; 57.7]<br>0.012 | 0.45 |
| 12 months, % [CI]<br>$p^3$-value | 30.2 [22.8; 37.6]<br>0.0001 | 39.6 [25.7; 53.4]<br>0.029 | 0.23 |
| ApoA1 | | | |
| 33 percentile, g/l baseline, % [CI] | <1.19<br>33.3 [31.8; 34.6] | <1.18<br>34.0 [21.2; 46.7] | |
| 3 months, % [CI]<br>$p^1$-value | 25.6 [18.8; 32.4]<br>0.0001 | 22.0 [10.5; 33.5]<br>0.003 | 0.604 |
| 6 months, % [CI]<br>$p^2$-value | 23.7 [16.5; 30.9]<br>0.0001 | 17.3 [7.0; 27.6]<br>0.001 | 0.34 |
| 12 months, % [CI]<br>$p^3$-value | 30.0 [22.7; 37.3]<br>0.0001 | 20.8 [9.3; 32.3]<br>0.004 | 0.22 |
| ApoB | | | |
| 66 percentile, g/l baseline, % [CI] | >1.02 g/l<br>33.3 [26.0; 40.6] | >0.98<br>32.1 [19.5; 44.7] | |
| 3 months, % [CI]<br>$p^1$-value | 36.3 [28.8; 43.7]<br>0.0002 | 42.0 [28.3; 55.7]<br>0.046 | 0.46 |
| 6 months, % [CI]<br>$p^2$-value | 30.4 [22.6; 38.1]<br>0.001 | 46.2 [32.6; 59.7]<br>0.012 | 0.042 |
| 12 months, % [CI]<br>$p^3$-value | 32.7 [25.2; 40.2]<br>0.0002 | 41.2 [27.2; 55.6]<br>0.032 | 0.26 |
| ApoB/A1 ratio | | | |
| 66 percentile baseline, % [CI] | >0.78<br>33.3 [26,1; 40.6] | >0.79<br>32.1 [19.5; 44.6] | |
| 3 months, % [CI]<br>$p^1$-value | 36.3 [28.8; 43.7]<br>0.0002 | 26.0 [13.8; 38.2]<br>0.010 | 0.18 |
| 6 months, % [CI]<br>$p^2$-value | 34.8 [26.8; 42.8]<br>0.006 | 26.9 [14.9; 39.0]<br>0.007 | 0.30 |
| 12 months, % [CI]<br>$p^3$-value | 32.0 [24.5; 39.5]<br>0.0002 | 31.3 [18.1; 44.4]<br>0.034 | 0.92 |

Frequency of patients is indicated as % [0.95 confidence interval].
$p^1$, $p^2$ and $p^3$ estimate changes between 0-3, 0-6 and 0-12 months respectively. $p^4$ estimates difference between treatment groups. p-values <0.05 are assumed to be statistically significant, marked as bold.
OxLDL = oxidized low-density lipoprotein, apoA1 = apolipoprotein A1, apoB = apolipoprotein B.

EXAMPLE 2

Inhibition of Lysophosphatidylcholine Induced Cell Death by Anti-PC IgM

Figure 3:
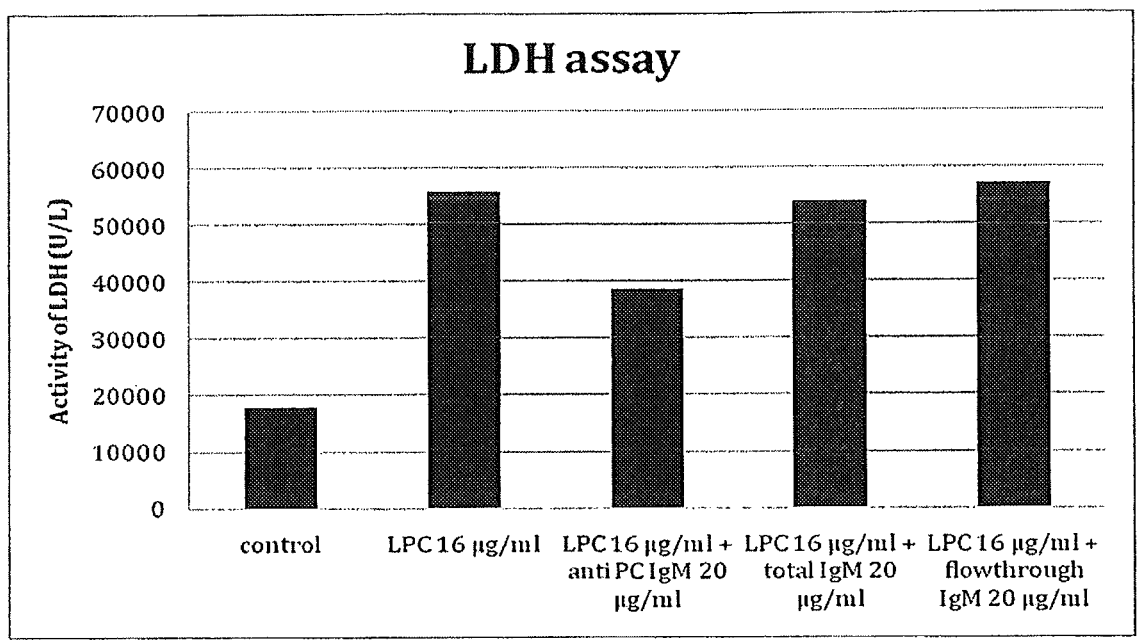
FIG. 3. Effect of antibodies against phosphorylcholine (anti-PC) IgM antibodies on lysophosphatidylcholine (LPC) induced necrosis, expressed as fluorescent measure of leakage of lactate dehydrogenase from cells with a damaged membrane in PBMC. (300,000 cells/well, 96 well plates) were incubated with LPC for 2 h and LDH activity in supernatant was measured. Anti-PC or control antibodies which did not bind PC, were preincubated with LPC 90 minutes before starting the treatment. The results were expressed as units per liter of LDH.

Peripheral blood mononuclear cells (PBMC) in 96 well plates (with 300,000 cells/well) were incubated with lysophosphatidylcholine (LPC) for 2 h, and cell death was assessed by measuring lactate dehydrogenase (LDH) activity in the supernatant. Antibodies against phosphorylcholine (anti-PC IgM) or control antibodies which did not bind PC, were preincubated with LPC 90 minutes before starting the treatment. The results were expressed as units per liter of LDH. As can be seen from FIG. 3, anti-PC IgM reduced cell death more than total IgM and flowthrough IgM.

Figure 4:
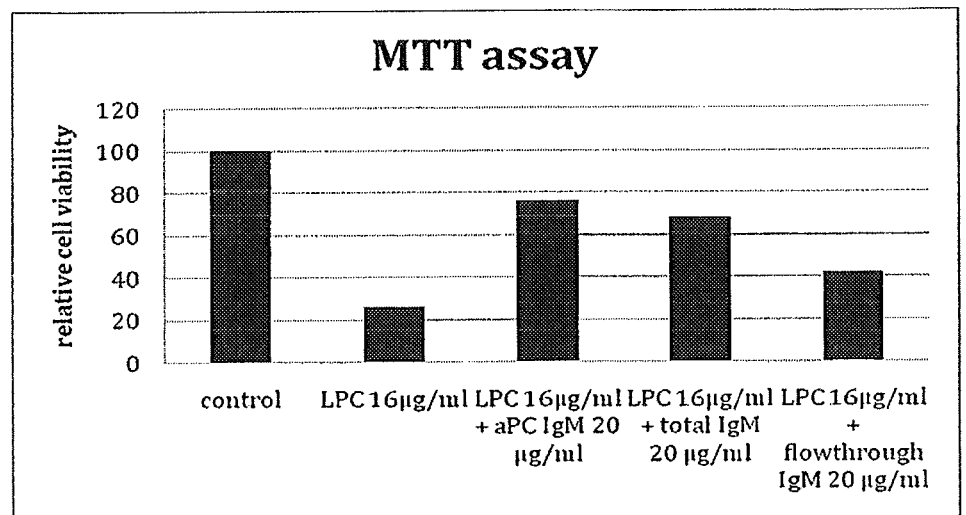
FIG. 4. Effect of human IgM antibodies on lysophosphatidylcholine (LPC) induced cytotoxicity, measured as decrease in mitochondrial dehydrogenaze activity in PBMC. (3,000,000 cells/well) were incubated with LPC for 18 h and the mitochondrial dependent reduction of MTT to formazin was measured. Anti-PC, total IgM and IgM which did not bind PC (flow through) were preincubated with LPC 90 minutes before starting the treatment. The results were expressed percentage of viable cells compared with non stimulated cells (control).

PBMC (3,000,000 cells/well) were incubated with LPC for 18 h, and cell death was assessed by measuring the decrease in mitochondrial dependent reduction of MTT to formazin. Anti-PC, total IgM and IgM which did not bind PC (flow through) were preincubated with LPC 90 minutes before starting the treatment. The results were expressed as percentage of viable cells compared with non-stimulated cells (control). As can be seen from FIG. 4, anti-PC IgM reduced cell death more than total IgM or flowthrough IgM.

EXAMPLE 3

Protective Effect of Combination of High Anti-PC with High Anti-MDA-LDL or High Anti-OxLDL ELSA-Study
Materials and Methods
Subjects Serum samples were obtained from 226 subjects with established hypertension (diastolic pressure>95 mm Hg) prior to their entry into the Swedish component of the European Lacidipine Study on Atherosclerosis (ELSA)[44,45]. Samples were collected following a 4-week washout period without medication to minimize the effects of treatment on the measured parameters. Blood pressure, cholesterol and triglyceride levels were determined as described previously[44,45] One hundred and fifteen of the subjects were subsequently assigned to treatment with the β-blocker atenolol, and 111 of the subjects were assigned to treatment with the calcium antagonist lacidipine.

Carotid ultrasound determinations were performed and analysed as detailed elsewhere[19,44,45]. A total of 226 patients had valid ultrasound measurements at baseline and after 4 years of follow up. Briefly, the right and left carotid arteries were examined with Biosound 2000 IIA duplex scanner using a 8.0 MHz annular array transducer. The intima-media (I-M) thickness was determined in the far wall as the distance between the leading edge of the lumen-intima echo and the leading edge of the media-adventitia echo. The outcome measurement as a surrogate indicator for atherosclerosis was the change in mean maximum Intimal-Medial thickness (IMT) of the four far walls in the distal common carotids and carotid bifurcations bilaterally (CBMmax) at the 4-year follow-up. The associations between antibody levels to PC at enrolment into the study with an increase or decrease in IMT at the 4-year follow-up were evaluated.

IgM antibodies to PC-BSA were determined by enzyme-linked immunosorbent assay (ELISA). Pooled serum from the same donors was used as an internal standard and tested on every plate. The plateau of antibody binding was reached with the antigen concentration of 10 µg/ml. F96 microtiter polysorp plate was therefore coated with PC-BSA (10 µg/ml) 50 µl/well in PBS. Coated plates were incubated overnight at 40 C. After five washings with PBS, the plates were blocked with 2% BSA-PBS for 2 h at room temperature and washed as described above. Serum samples were diluted (1:30) in 0.2% BSA-PBS and added at 50 µl/well.

LDL was isolated from plasma of healthy donors by sequential preparative ultra-centrifugation and oxidized by use of copper ions (OxLDL) or derivatized with MDA (MDA-LDL) as described[11]. OxLDL and MDA-LDL were determined by ELISA essentially as described[11]. OxLDL or MDA-LDL was diluted to 2 µg/ml in coating buffer (carbonate-bicarbonate buffer 50 mM pH 9.7), and 100 µl/well was used to coat ELISA plates (Costar 2581). The plates were kept at 4° C. overnight, washed 4 times with PBS, and then blocked with 20% adult bovine serum in PBS (20% ABS-PBS) for 2 hours in room temperature. They were then incubated with 100 µl serum, diluted 1:30 in 20% ABS-PBS at 4° C. overnight.

Plates were incubated overnight at 4° C. and washed as described above. Alkaline phosphatase conjugated goat anti-human IgG (diluted 1:9000 in the sample buffer) and Alkaline phosphatase conjugated goat anti-human IgM (diluted 1:7000 in the sample buffer) were added at 100 ul/well and incubated at 4° C. overnight. After five washings, color was developed by adding the Alkaline phosphatase substrate (PNPP) at 100 ul/well and incubating the plates for 60 min at room temperature in the dark. The plates were read in an ELISA Multiskan Plus spectrophotometer (Molecular Devices Emax, San Francisco) at 405 nm. All samples were measured in a single assay and the coefficient of variation was below 10-15%.

Results

Details of the study on Basic characteristics and anti-PC, anti-OxLDL and anti-MDA-LDL separately has been presented elsewhere[19].

When high anti-MDA-LDL and high anti-PC (both IGM) or high anti-OxLDL and high anti-PC (both IgM) where combined, surprisingly, the associations with decreased development of atherosclerosis (protection effect) were strongly and significantly raised (table 6).

CONCLUSION

Anti-PC IgM as a protection factor becomes stronger when combined with anti-MDA-LDL or anti-OxLDL, suggesting that a combination of these antibodies, raised through active immunization (vaccination) or passive immunization (where antibodies are administered), has advantages as compared to single therapies.

TABLE 5

Basic characteristics of the study group at enrolment. Results are presented as means (SD) or percentage (%) and mg/dL for lipids.

|  | Total (N = 226) | Atenolol (N = 115) | Lacidipine (N = 111) |
|---|---|---|---|
| Age (years) | 57.7 (7.8) | 57.6 (7.6) | 57.7 (7.9) |
| Sex (% males) | 50 | 46 | 53 |
| BMI | 26.7 (3.7) | 26.3 (3.3) | 27.1 (3.9) |
| Total Cholesterol | 232.4 (37.8) | 233.5 (38.1) | 231.4 (37.4) |
| HDL | 55.6 (27.6) | 56.5 (25.8) | 54.7 (27.6) |
| LDL | 149.4 (37.8) | 149.7 (37.1) | 149.2 (38.6) |
| Triglycerides | 131.6 (58.2) | 128.6 (57.0) | 134.7 (59.5) |

TABLE 6 prediction of changes in IMT with baseline levels of IgM autoantibodies to phosphorylcholine (PC) or MDA-LDL.

| Variable | Odds Ratio | (95% CI) Lower | (95% CI) Upper | p |
|---|---|---|---|---|
| aMDA-LDL (highest 25$^{th}$ percentile | .67 | .36 | 1.2 | .18 |
| Anti-PC (highest 10$^{th}$ percentile) | .36 | .15 | 0.87 | .024 |
| aMDA-LDL(IgM) and anti-PC (combined) | .14 | .038 | 0.512 | .003 |

TABLE 7 prediction of changes in IMT with baseline levels of IgM autoantibodies to phosphorylcholine (PC) or Ox-LDL.

| Variable | Odds Ratio | (95% CI) Lower | (95% CI) Upper | p |
|---|---|---|---|---|
| aOx-LDL (highest 25$^{th}$ percentile | .84 | 0.46 | 1.56 | 0.4 |
| Anti-PC (highest 10$^{th}$ percentile) | .36 | .15 | 0.87 | .024 |

TABLE 7-continued prediction of changes in IMT with baseline levels of IgM autoantibodies to phosphorylcholine (PC) or Ox-LDL.

| Variable | Odds Ratio | (95% CI) Lower | (95% CI) Upper | p |
|---|---|---|---|---|
| aOx-LDL(IgM) and anti-PC (as above, combined) | .12 | .033 | 0.42 | .003 |

EXAMPLE 4

Increased Risk of CVD from Combination of Low IgM Anti-PC with Low Anti-OxCL or Low Anti-OxPS Study of 60-Year Olds
Objective.

We here determine the role of IgM antibodies against phosphorylcholine (anti-PC) in combination with antibodies against oxidized cardiolipin (anti-OxCL) or antibodies against oxidized phosphatidylserine (anti-OxPS) in prediction of cardiovascular disease (CVD).

Methods.

From a screening of 4232 subjects, 60-years old (2039 men and 2193 women), 211 incident cases of CVD (myocardial infarction, ischemic stroke, or hospitalized angina pectoris) and 633 age- and sex-matched controls were identified through a 5-7 year follow-up[18,46,47]. Serum levels of antibodies was determined by ELISA. Cardiolipin and phosphatidylserine was oxidized in aqueous solutions containing 1.5 mmol/L tert-butylhydroperoxide and $CuSO_4$ in 20 µmol/L.

Results.

In women, there were no significant associations between anti-PC and CVD. Among men, individuals with anti-PC levels in lowest quartile 4 (lowest) as the reference value yielded a trendwise excess risk for CVD (p=0.069) which was not significant. However when combined with low anti-OxCL or low anti-OxPS (both below 25th percentile), associations became significant with an increase from p=0.069 to p=0.042 (when combined with anti-OxCL) and 0.024 (when combined with anti-OxPS).

Conclusions.

A combination of low IgM anti-PC with low anti-OxCL or low anti-OxPS increases the excess risk of CVD. A combination of these antibodies could improve therapy, if raised through active immunization or passive immunization. All references as listed below and discussed in the above description are hereby incorporated by reference in their entirety.

REFERENCES

1. Weinblatt M E, Kuritzky L. RAPID: rheumatoid arthritis. *J Fam Pract.* 2007; 56(4 Suppl):S1-7; quiz S8.
2. Meune C, Touze E, Trinquart L, Allanore Y. Trends in cardiovascular mortality in patients with rheumatoid arthritis over 50 years: a systematic review and meta-analysis of cohort studies. *Rheumatology (Oxford).* 2009; 48(10):1309-1313.
3. Peters M J, van Halm V P, Voskuyl A E, Smulders Y M, Boers M, Lems W F, Visser M, Stehouwer C D, Dekker J M, Nijpels G, Heine R, Dijkmans B A, Nurmohamed M T. Does rheumatoid arthritis equal diabetes mellitus as an independent risk factor for cardiovascular disease? A prospective study. *Arthritis Rheum.* 2009; 61(11):1571-1579.
4. Frostegard J. Atherosclerosis in patients with autoimmune disorders. *Arterioscler Thromb Vasc Biol.* 2005; 25(9): 1776-1785.
5. Cugno M, Ingegnoli F, Gualtierotti R, Fantini F. Potential effect of anti-tumour necrosis factor-alpha treatment on reducing the cardiovascular risk related to rheumatoid arthritis. *Curr Vasc Pharmacol.* 2010 March; 8(2):285-92.
6. Maki-Petaja K M, Hall F C, Booth A D, Wallace S M, Yasmin, Bearcroft P W, Harish S, Furlong A, McEniery C M, Brown J, Wilkinson I B. Rheumatoid arthritis is associated with increased aortic pulse-wave velocity, which is reduced by anti-tumor necrosis factor-alpha therapy. *Circulation.* 2006; 114(11):1185-1192.
7. Van Doornum S, McColl G, Wicks I P. Tumour necrosis factor antagonists improve disease activity but not arterial stiffness in rheumatoid arthritis. *Rheumatology (Oxford).* 2005; 44(11):1428-1432.
8. Garces S P, Parreira Santos M J, Vinagre F M, Roque R M, da Silva J A. Anti-tumour necrosis factor agents and lipid profile: a class effect? *Ann Rheum Dis.* 2008; 67(6): 895-896.
9. Soubrier M, Jouanel P, Mathieu S, Poujol D, Claus D, Dubost J J, Ristori J M. Effects of anti-tumor necrosis factor therapy on lipid profile in patients with rheumatoid arthritis. *Joint Bone Spine.* 2008; 75(1):22-24.
10. Dorner T, Radbruch A, Burmester G R. B-cell-directed therapies for autoimmune disease. *Nat Rev Rheumatol.* 2009; 5(8):433-441.
11. Wu R, de Faire U, Lemne C, Witztum J L, Frostegard J. Autoantibodies to OxLDL are decreased in individuals with borderline hypertension. *Hypertension.* 1999; 33(1): 53-59.
12. Binder C J, Silverman G J. Natural antibodies and the autoimmunity of atherosclerosis. *Springer Semin Immunopathol.* 2005; 26(4):385-404.
13. Shoenfeld Y, Wu R, Dearing L D, Matsuura E. Are anti-oxidized low-density lipoprotein antibodies pathogenic or protective? *Circulation.* 2004; 110(17):2552-2558.
14. Kerekes G, Soltesz P, Der H, Veres K, Szabo Z, Vegvari A, Szegedi G, Shoenfeld Y, Szekanecz Z. Effects of rituximab treatment on endothelial dysfunction, carotid atherosclerosis, and lipid profile in rheumatoid arthritis. *Clin Rheumatol.* 2009; 28(6):705-710.
15. Jin T, Bokarewa M, Amu S, Tarkowski A. Impact of short-term therapies with biologics on prothrombotic biomarkers in rheumatoid arthritis. *Clin Exp Rheumatol.* 2009; 27(3):491-494.
16. Gronlund H, Hallmans G, Jansson J H, Boman K, Wikstrom M, de Faire U, Frostegard J. Low levels of IgM antibodies against phosphorylcholine predict development of acute myocardial infarction in a population-based cohort from northern Sweden. *Eur J Cardiovasc Prev Rehabil.* 2009.
17. Elkan A C, Sjoberg B, Kolsrud B, Ringertz B, Hafstrom I, Frostegard J. Gluten-free vegan diet induces decreased LDL and oxidized LDL levels and raised atheroprotective natural antibodies against phosphorylcholine in patients with rheumatoid arthritis: a randomized study. *Arthritis Res Ther.* 2008; 10 (2):R34.
18. de Faire U, Su J, Hua X, Frostegard A, Halldin M, Hellenius M L, Wikstrom M, Dahlbom I, Gronlund H, Frostegard J. Low levels of IgM antibodies to phosphorylcholine predict cardiovascular disease in 60-year old men: Effects on uptake of oxidized LDL in macrophages as a potential mechanism. *J Autoimmun.* 2009.
19. Su J, Georgiades A, Wu R, Thulin T, de Faire U, Frostegard J. Antibodies of IgM subclass to phosphorylcholine and oxidized LDL are protective factors for atherosclerosis in patients with hypertension. *Atherosclerosis.* 2006; 188(1):160-166.
20. Su J, Hua X, Concha H, Svenungsson E, Cederholm A, Frostegard J. Natural antibodies against phosphorylcholine as potential protective factors in SLE. *Rheumatology (Oxford).* 2008; 47(8):1144-1150.
21. Cornec D, Avouac J, Youinou P, Saraux A. Critical analysis of rituximab-induced serological changes in connective tissue diseases. *Autoimmun Rev.* 2009; 8(6):515-519.
22. Briles D E, Forman C, Hudak S, Claflin J L. Antiphosphorylcholine antibodies of the T15 idiotype are optimally protective against *Streptococcus pneumoniae. J Exp Med.* 1982; 156(4):1177-1185.
23. Harnett W, Harnett M M. Phosphorylcholine: friend or foe of the immune system? *Immunol Today.* 1999; 20(3):125-129.
24. Frostegard J, Tao W, Georgiades A, Rastam L, Lindblad U, Lindeberg S. Atheroprotective natural anti-phosphorylcholine antibodies of IgM subclass are decreased in Swedish controls as compared to non-westernized individuals from New Guinea. *Nutr Metab (Lond).* 2007; 4(1):7.
25. Caligiuri G, Khallou-Laschet J, Vandaele M, Gaston A T, Delignat S, Mandet C, Kohler H V, Kaveri S V, Nicoletti A. Phosphorylcholine-targeting immunization reduces atherosclerosis. *J Am Coll Cardiol.* 2007; 50(6):540-546.
26. Faria-Neto J R, Chyu K Y, Li X, Dimayuga P C, Ferreira C, Yano J, Cercek B, Shah P K. Passive immunization with monoclonal IgM antibodies against phosphorylcholine reduces accelerated vein graft atherosclerosis in apolipoprotein E-null mice. *Atherosclerosis.* 2006; 189(1):83-90.
27. Edwards L J, Constantinescu C S. Platelet activating factor/platelet activating factor receptor pathway as a potential therapeutic target in autoimmune diseases. *Inflamm Allergy Drug Targets.* 2009; 8(3):182-190.
28. Gonzalez-Juanatey C, Llorca J, Vazquez-Rodriguez T R, Diaz-Varela N, Garcia-Quiroga H, Gonzalez-Gay M A. Short-term improvement of endothelial function in rituximab-treated rheumatoid arthritis patients refractory to tumor necrosis factor alpha blocker therapy. *Arthritis Rheum.* 2008; 59(12):1821-1824.
29. Reff M E, Carner K, Chambers K S, Chinn P C, Leonard J E, Raab R, Newman R A, Hanna N, Anderson D R. Depletion of B cells in vivo by a chimeric mouse human monoclonal antibody to CD20. *Blood.* 1994; 83(2):435-445.
30. van Leeuwen M, Damoiseaux J, Duijvestijn A, Tervaert J W. The therapeutic potential of targeting B cells and anti-oxLDL antibodies in atherosclerosis. *Autoimmun Rev.* 2009; 9(1):53-57.
31. Cambridge G, Leandro M J, Teodorescu M, Manson J, Rahman A, Isenberg D A, Edwards J C. B cell depletion therapy in systemic lupus erythematosus: effect on autoantibody and antimicrobial antibody profiles. *Arthritis Rheum.* 2006; 54(11):3612-3622.
32. Frostegard J, Wu R, Giscombe R, Holm G, Lefvert A K, Nilsson J. Induction of T-cell activation by oxidized low density lipoprotein. *Arterioscler Thromb.* 1992; 12(4):461-467.
33. Winyard P G, Tatzber F, Esterbauer H, Kus M L, Blake D R, Morris C J. Presence of foam cells containing oxidized low density lipoprotein in the synovial membrane from patients with rheumatoid arthritis. *Ann Rheum Dis.* 1993; 52(9):677-680.
34. Suzuki T, Kohno H, Hasegawa A, Toshima S, Amaki T, Kurabayashi M, Nagai R, Suzuki T, Amaki T, Nagai R, Hasegawa A, Toshima S, Kurabayashi M H, Shimada K, Nakamura H, Teramoto T, Yamaguchi H, Nishiyama S, Takahashi H, Michishita I, Sugano Z, Konoshi K. Diagnostic implications of circulating oxidized low density lipoprotein levels as a biochemical risk marker of coronary artery disease. *Clin Biochem.* 2002; 35(5):347-353.
35. Itabe H, Ueda M. Measurement of plasma oxidized low-density lipoprotein and its clinical implications. *J Atheroscler Thromb.* 2007; 14(1):1-11.
36. Holme I, Aastveit A H, Hammar N, Jungner I, Walldius G. Lipoprotein components and risk of congestive heart failure in 84,740 men and women in the Apolipoprotein MOrtality RISk study (AMORIS). *Eur J Heart Fail.* 2009; 11(11):1036-1042.
37. Walldius G, Jungner I. Rationale for using apolipoprotein B and apolipoprotein A-I as indicators of cardiac risk and as targets for lipid-lowering therapy. *Eur Heart J.* 2005; 26(3):210-212.
38. Choy E, Sattar N. Interpreting lipid levels in the context of high-grade inflammatory states with a focus on rheumatoid arthritis: a challenge to conventional cardiovascular risk actions. *Ann Rheum Dis.* 2009; 68(4):460-469.
39. Jacobsson L T, Turesson C, Nilsson J A, Petersson I F, Lindqvist E, Saxne T, Geborek P. Treatment with TNF blockers and mortality risk in patients with rheumatoid arthritis. *Ann Rheum Dis.* 2007; 66(5):670-675.
40. Arnett F C, Edworthy S M, Bloch D A, McShane D J, Fries J F, Cooper N S, Healey L A, Kaplan S R, Liang M H, Luthra H S, et al. The American Rheumatism Association 1987 revised criteria for the classification of rheumatoid arthritis. *Arthritis Rheum.* 1988; 31(3):315-324.
41. Prevoo M L, van't Hof M A, Kuper H H, van Leeuwen M A, van de Putte L B, van Riel P L. Modified disease activity scores that include twenty-eight-joint counts. Development and validation in a prospective longitudinal study of patients with rheumatoid arthritis. *Arthritis Rheum.* 1995; 38(1):44-48.
42. Ekdahl C, Eberhardt K, Andersson S I, Svensson B. Assessing disability in patients with rheumatoid arthritis. Use of a Swedish version of the Stanford Health Assessment Questionnaire. *Scand J Rheumatol.* 1988; 17(4):263-271.
43. Sjoberg B G, Su J, Dahlbom I, Gronlund H, Wikstrom M, Hedblad B, Berglund G, de Faire U, Frostegard J. Low levels of IgM antibodies against phosphorylcholine-A potential risk marker for ischemic stroke in men. *Atherosclerosis.* 2009; 203(2):528-532.
44. Zanchetti A, Bond M G, Hennig M, Neiss A, Mancia G, Dal Palu C, Hansson L, Magnani B, Rahn K H, Reid J, Rodicio J, Safar M, Eckes L, Ravinetto R. Risk factors associated with alterations in carotid intima-media thickness in hypertension: baseline data from the European Lacidipine Study on Atherosclerosis. *J Hypertens.* 1998; 16(7):949-961.

45. Zanchetti A, Bond M G, Hennig M, Neiss A, Mancia G, Dal Palu C, Hansson L, Magnani B, Rahn K H, Reid J L, Rodicio J, Safar M, Eckes L, Rizzini P. Calcium antagonist lacidipine slows down progression of asymptomatic carotid atherosclerosis: principal results of the European Lacidipine Study on Atherosclerosis (ELSA), a randomized, double-blind, long-term trial. *Circulation.* 2002; 106(19):2422-2427.

46. Carlsson A C, Wandell P E, de Faire U, Hellenius M L. Risk factors associated with newly diagnosed high blood pressure in men and women. Am J Hypertens. 2008; 21(7):771-777.

46. Halldin M, Rosell M, de Faire U, Hellenius M L. The metabolic syndrome: prevalence and association to leisure-time and work-related physical activity in 60-year-old men and women. Nutr Metab Cardiovasc Dis. 2007; 17(5):349-357.

The invention claimed is:

1. A method for increasing the efficacy of infliximab in a non-responder mammal to infliximab for curing, treating, preventing, and/or reducing the risk of developing rheumatoid arthritis, said method comprising:
    identifying an individual that is a non-responder to infliximab; and
    administering infliximab in combination with antibodies or derivatives thereof against PC or PC conjugate thereof to the non-responder,
    wherein said antibodies or derivatives thereof against PC or PC conjugate is selected from the group comprising a monoclonal, polyclonal or chimeric antibody of isotype IgA, IgD, IgE, IgG, IgM, optionally in combination with any suitable excipients or adjuvants; and
    wherein said mammal is selected from the group comprising rabbits, dogs, cats, horses and humans.

2. The method of claim 1, wherein administering the infliximab comprises co-administering infliximab simultaneously with the antibodies or derivatives thereof against PC or PC conjugate thereof.

* * * * *